United States Patent
Zenhausern et al.

(10) Patent No.: US 12,426,815 B2
(45) Date of Patent: Sep. 30, 2025

(54) INTEGRATED DEVICE FOR SELF-COLLECTING AND AUTOMATED PRE-PROCESSING OF BIOLOGICAL FLUIDS

(71) Applicant: Arizona Board of Regents on Behalf of the University of Arizona, Tucson, AZ (US)

(72) Inventors: Frederic Zenhausern, Phoenix, AZ (US); Jian Gu, Phoenix, AZ (US); Alan Nordquist, Phoenix, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 1009 days.

(21) Appl. No.: 17/044,172

(22) PCT Filed: Apr. 26, 2019

(86) PCT No.: PCT/US2019/029385
§ 371 (c)(1),
(2) Date: Sep. 30, 2020

(87) PCT Pub. No.: WO2019/210195
PCT Pub. Date: Oct. 31, 2019

(65) Prior Publication Data
US 2021/0030347 A1      Feb. 4, 2021

Related U.S. Application Data

(60) Provisional application No. 62/663,515, filed on Apr. 27, 2018.

(51) Int. Cl.
*A61B 5/15*     (2006.01)
*A61B 5/151*    (2006.01)
*A61B 5/157*    (2006.01)

(52) U.S. Cl.
CPC .. *A61B 5/150755* (2013.01); *A61B 5/150099* (2013.01); *A61B 5/150251* (2013.01);
(Continued)

(58) Field of Classification Search
CPC ........ A61B 5/150755; A61B 5/150099; A61B 5/150251; A61B 5/150343;
(Continued)

(56) References Cited

U.S. PATENT DOCUMENTS

| 4,326,541 A | 4/1982 | Eckels |
| 10,898,896 B2 | 1/2021 | Zenhausern et al. |

(Continued)

FOREIGN PATENT DOCUMENTS

| EP | 0073551 A2 | 3/1983 |
| WO | WO 2011/127056 A2 | 10/2011 |

(Continued)

OTHER PUBLICATIONS

Bowen et al. (2010) "Impact of blood collection devices on clinical chemistry assays," Clin. Biochem. 43, 4-25.
(Continued)

*Primary Examiner* — Tse W Chen
*Assistant Examiner* — Evelyn Grace Park
(74) *Attorney, Agent, or Firm* — Leydig, Voit & Mayer, Ltd.

(57) ABSTRACT

Provided is an integrated sample collection device for self-collection and analytical pre-processing of a fluid sample, such as a blood sample from a user. A housing is configured to be held by a user, such as a single hand of a user. A contact-activated penetrating member is disposed at least partially in the housing and configured to penetrate skin. A capillary tube is disposed at least partially in the housing and configured to collect blood released by the penetrating member that penetrates the skin. A vacuum-assisted blood (Continued)

collection container can be fluidically connected to the capillary tube for receiving at least a portion of the collected blood. One or more stabilizing/pre-processing agents are provided for stabilizing/pre-processing collected blood in the capillary tube, the vacuum-assisted blood storage container, or both.

23 Claims, 19 Drawing Sheets

(52) U.S. Cl.
CPC .. *A61B 5/150343* (2013.01); *A61B 5/150419* (2013.01); *A61B 5/15109* (2013.01); *A61B 5/157* (2013.01)

(58) Field of Classification Search
CPC .......... A61B 5/150419; A61B 5/15109; A61B 5/157; B01L 3/502; G01N 33/49; G01N 33/491
See application file for complete search history.

(56) References Cited

U.S. PATENT DOCUMENTS

| | | | |
|---|---|---|---|
| 11,221,966 B2 | 1/2022 | Zenhausern et al. | |
| 2004/0127816 A1 | 7/2004 | Galvao | |
| 2010/0150423 A1* | 6/2010 | Hong | G06V 10/267 382/133 |
| 2012/0149004 A1* | 6/2012 | Gelfand | A61B 5/150351 422/549 |
| 2013/0209985 A1 | 8/2013 | Hoke et al. | |
| 2014/0073992 A1 | 3/2014 | Hufford et al. | |
| 2016/0256095 A1 | 9/2016 | Krasnow et al. | |
| 2017/0122846 A1* | 5/2017 | Holmes | G01N 33/491 |
| 2019/0345431 A1 | 11/2019 | Barrett et al. | |
| 2021/0079337 A1 | 3/2021 | Zenhausern et al. | |
| 2021/0199651 A1 | 7/2021 | Zenhausern et al. | |
| 2022/0001378 A1 | 1/2022 | Zenhausern et al. | |

FOREIGN PATENT DOCUMENTS

| | | |
|---|---|---|
| WO | WO 2020/264385 A1 | 12/2020 |
| WO | WO 2020/264388 A1 | 12/2020 |

OTHER PUBLICATIONS

Bush et al. (1998) "Advancements in Blood Collection Devices," Lab. Med., 29, 616-622.
Bush et al. (2003) "The evolution of evacuated blood collection tubes," Lab Med. 34(4):304-310.
Chai et al. (2005) "Optimization of the PAXgene™ blood RNA extraction system for gene expression analysis of clinical samples," J. Clin. Lab. Anal., 19, 182-188.
Chen et al. (2010) "An integrated, self-contained microfluidic cassette for isolation, amplification, and detection of nucleic acids," Biomed Microdevices, 12(4):705-719.
Coleman et al. (2009) "Medical Response to a Radiologic/Nuclear Event: Integrated Plan From the Office of the Assistant Secretary for Preparedness and Response, Department of Health and Human Services," Ann Emerg Med., 53(2):213-22.
Cytogenetic Dosimetry: Applications in Preparedness for and Response to Radiation Emergencies (2011) International Atomic Energy Agency, Vienna. 247 pp.
Czurratis et al. (2015) "Liquids on-chip: direct storage and release employing micro-perforated vapor barrier films," Lab Chip, 15(13):2887-2895.
DuPont (1992) Design Handbook for DuPont Engineering Polymers, Module 1: General Design Principles, 153 pp.
Grace et al. (2010) "Rapid Radiation Dose Assessment for Radiological Public Health Emergencies: Roles of Niaid and Barda," Health Phys.; 98(2):172-178.
Gu et al. (Oct. 2019) "Development of an integrated fingerstick blood self-collection device for radiation countermeasures," PLoS One 14(10: e0222951. https://doi.org/10.1371/journal.pone. 0222951.
Hirshfield et al. (Nov. 2018) "Quantification of HIV-1 RNA Among Men Who Have Sex With Men Using an At-Home Self-Collected Dried Blood Spot Specimen: Feasibility Study," JMIR Public Health Surveill.; 4(4):e10847.
Hoffmann et al. (2010) "Pre-storage of liquid reagents in glass ampoules for DNA extraction on a fully integrated lab-on-a-chip cartridge," Lab Chip, 10, 1480-1484.
International Search Report and Written Opinion, dated Jul. 10, 2019 in International Application No. PCT/US2019/029385, 15 pp.
Komatsuka et al. (2009) "Temperature Dependence on Gas Permeability and Permselectivity of Poly(lactic acid) Blend Membranes," Polym J.; 41(5):455-458.
Li et al. (2015) "A self-powered one-touch blood extraction system: a novel polymer-capped hollow microneedle integrated with a pre-vacuum actuator," Lab Chip, 15(2):382-390.
MacNutt et al. (2008) "Performance of evacuated blood collection tubes at high altitude," High Alt Med Biol. 9(3):235-237.
Matsunaga et al. (2005) "Gas Permeability of Thermoplastic Polyurethane Elastomers," Polym. J., 37, 413-417.
Paul et al. (2008) "Development of gene expression signatures for practical radiation biodosimetry," Int J Radiat Oncol Biol Phys.; 71(4):1236-1244.
Repin et al. (Apr. 2017) "RABiT-II: Implementation of a High-Throughput Micronucleus Biodosimetry Assay on Commercial Biotech Robotic Systems," Radiat Res. 187(4):502-508.
Repin et al. (Mar. 2019) "RABiT-II: A Fully-Automated Micronucleus Assay System with Shortened Time to Result," Radiat Res. 191(3):232-236.
Sawano et al. (2008) "Sealing method of PDMS as elastic material for MEMS," 2008 IEEE 21st International Conference on Micro Electro Mechanical Systems, 419-422.
Shah et al. (Oct. 2017) "Video instruction is more effective than written instruction in improving inhaler technique," Pulm Pharmacol Ther.; 46:16-19.
Sullivan et al. (2013) "Assessment of Biodosimetry Methods for a Mass-Casualty Radiological Incident: Medical Response and Management Considerations," Health Phys. 105(6):540-54.
Swartz et al. (2010) "A Critical Assessment of Biodosimetry Methods for Large-Scale Incidents," Health Phys., 98, 95-108.
Van Amerongen (1946) "The Permeability of Different Rubbers to Gases and its Relation to Diffusivity and Solubility," J Appl Phys.; 17(11):972-985.
Van Oordt et al. (2013) "Miniature stick-packaging—an industrial technology for pre-storage and release of reagents in lab-on-a-chip systems," Lab Chip, 13, 2888-2892.
Xu et al. (2015) "Vacuum-driven power-free microfluidics utilizing the gas solubility or permeability of polydimethylsiloxane (PDMS)," Lab Chip.; 15(20):3962-3979.

* cited by examiner

INTEGRATED DEVICE FOR SELF-COLLECTING AND AUTOMATED PRE-PROCESSING OF BIOLOGICAL FLUIDS

CROSS-REFERENCE TO RELATED APPLICATIONS

This application is a U.S. National Stage Application filed under 35 U.S.C § 371 of International Application No. PCT/US2019/029385, filed Apr. 26, 2019 which claims the benefit of U.S. Provisional Application No. 62/663,515, filed on Apr. 27, 2018, which is incorporated by reference herein in its entirety.

STATEMENT REGARDING FEDERALLY SPONSORED RESEARCH OR DEVELOPMENT

This invention was made with government support under Grant No. AI067773 awarded by the National Institutes of Health. The government has certain rights in this invention.

BACKGROUND OF INVENTION

Provided herein are medical devices for collection, stabilization, and preparation of biological fluids, including whole blood, during transportation to laboratory facilities equipped for clinical testing, for example, hematology and RNA assay testing. An example of the device is a NUCLE-AIR (Numerous Capillaries Lancet Emergency Assays for In-Route processing) device that is a point-of-contact system for the self-collection of multiple blood sample volumes (by trained healthcare worker or untrained layperson or individual him/herself) from a finger-stick or other skin areas.

The devices and methods provided herein address the need in the art for an efficient and accurate measure of one or more biological fluid parameters. Blood is a particularly useful biological fluid as it contains biological constituents, including cells, biomarkers and other biocomponents that can provide information about a wide range of biological conditions. For example, in a nuclear or radiological incident, whole blood samples can be used as a base indicator of radiological exposure based on a number of measureable parameters. There is need in the art, however, for reliable blood collection aligned, in a pre-processing type configuration, with subsequent laboratory processing and analysis. In this manner, the time required for the end-read out from a laboratory can be significantly reduced. Furthermore, the devices and systems presented herein are capable of being used by the person whose blood is being collected, without a need for any other persons, including medical personal. Accordingly, large numbers of samples can be reliably, efficiently, and accurately obtained without having to deploy a corresponding large number of personal to obtain the samples efficiently.

SUMMARY OF THE INVENTION

The devices and methods provided herein address the problems associated with accurate, efficient and timely biological fluid analysis by specially integrating blood collection, storage and pre-processing components in an integrated and user-friendly device. The device is compatible with multiplex analysis by collecting a plurality of blood samples, pre-processing them during travel to a laboratory, with subsequent independent analysis of each of the collected samples, thereby decreasing the total time the sample is spent at the laboratory to effectively reduce laboratory read-out time.

Provided is an integrated sample collection device for self-collection of a blood sample from a user. The device may have a housing configured to be held by a user, so that the user is capable of self-collecting a blood sample, Of course, the devices provided herein may be used by another to collect blood from the user. A contact-activated penetrating member is disposed at least partially in the housing and configured to penetrate skin. A capillary tube is at least partially disposed in the housing and configured to collect blood released from the penetrating member that penetrates the skin. The capillary tube may have a distal end that extends out of the housing to facilitate alignment of the capillary tube with a blood droplet on the skin. A vacuum-assisted blood collection container (also referred herein as a "VacuStor" tube or container) is fluidically connected to the capillary tube for receiving at least a portion of the collected blood. This fluidic connection may be temporary, such as by actuation to bring the capillary tube and collection container in fluidic contact to force the blood from the capillary tube to the collection container. One or more stabilizing/pre-processing agents for stabilizing/pre-processing collected blood may be provided in the device, such as in the capillary tube, the vacuum-assisted blood collection container, or both.

Any of the devices provided herein may be used in a method of sampling a blood sample. In particular, the ease of use of the device, without any active electronic components, makes the device ideally suited for use by a user in the field. Furthermore, as described herein, the multiple collected blood samples are configured to undergo a type of auto-preprocessing depending on the subsequent laboratory-run assay, so that downstream analytical and sample preparation time is improved.

Any of the devices provided herein may be characterized as having multiplex capability, being compatible with multiple analytical laboratory assays. For example, in the radiation context, the collected blood samples may be for use with three standard assays for radiobiological markers. The laboratory may use a high-throughput biodosimetry instrument platform, including for example RABIT cytogenetic assay, RT-PCR gene expression and/or LC/MS mass spectrometry.

The methods and devices provided herein not only integrate the various necessary components to reliably obtain a fluid sample, such as whole blood, but are configured to further extend the system beyond fluid sample preservation to a more activation type state tailored to a subsequent analytical process and direct processing of the fluid sample at the delivery site.

Representative embodiments of the invention include, but are not limited to:

1. An integrated sample collection device for self-collection and analytical pre-processing of a biological fluid sample from a user comprising: a housing configured to be held by a user; a contact-activated penetrating member disposed at least partially in the housing and configured to penetrate skin; a capillary tube at least partially disposed in the housing and configured to collect blood released from the penetrating member that penetrates the skin; a vacuum-assisted blood collection container fluidically connected to the capillary tube for receiving at least a portion of the collected blood; and one or more stabilizing and/or pre-processing agents for initiating an analytical pre-processing of the collected blood in the capillary tube, the vacuum-assisted blood collection container, or both.

2. The integrated sample collection device of embodiment 1 that is a multiple sample collection device further comprising: a plurality of capillary tubes; and a plurality of blood collection containers, with each individual capillary tube fluidically connected to a unique individual blood collection container.

3. The integrated sample collection device of any of embodiments 1-2, further comprising a plurality of contact-activated penetrating members configured to penetrate skin at a plurality of distinct locations, wherein the plurality of contact-activated penetrating members correspond to a lancet array.

4. The integrated sample collection device of embodiments 1-3, further comprising a plurality of capillary tubes to collect blood from a plurality of distinct skin locations and/or to store blood in a plurality of distinct vacuum-assisted blood collection storage containers.

5. The integrated sample collection device of any of embodiments 1-4, comprising: a first collection container configured for a first blood-based assay; a second collection container configured for a second blood-based assay; and a third collection container configured for a third blood-based assay.

6. The integrated sample collection device of embodiment 5, wherein the first blood-based assay is a cytogenetic assay, the second blood-based assay is a gene expression assay, and the third blood-based assay is a biomarker detection assay.

7. The integrated sample collection device of any of embodiments 1-6, wherein the collected blood sample is configured for use in a cell culture, an ELISA, RNA detection, DNA detection, protein detection, polypeptide detection, small molecule or metabolite profiling, gene expression measurement, microscopic or spectroscopic inspection.

8. The integrated sample collection device of any of embodiments 1-7, wherein the collection containers are configured to provide pre-processing during blood sample shipping in the collection container to a laboratory to decrease laboratory processing time.

9. The integrated device of any of embodiments 1-8, wherein at least one blood collection container comprises: a solid phase absorption member; or an extraction substrate.

10. The integrated sample collection device of any of embodiments 1-9, wherein the one or plurality of blood collection containers are removably connected to the housing.

11. The integrated sample collection device of any of embodiments 1-10, wherein a plurality of the vacuum-assisted blood storage containers are positioned in a container holder, and the container holder with the containers are configured for insertion into and removal from the housing.

12. The integrated sample collection device of any of embodiments 1-11, further comprising one or more blood storage containers operably connected to the vacuum-assisted blood collection container, wherein blood from the vacuum-assisted blood collection container is introduced to a blood storage container, including a blood storage container comprising a solid-phase substrate such as a membrane.

13. The integrated sample collection device of any of embodiments 1-12, further comprising: a needle connected to a proximal end the capillary tube configured to controllably pierce a cap of the vacuum-assisted blood storage container to thereby fluidically connect the capillary tube to the vacuum-assisted blood storage container.

14. The integrated sample collection device of any embodiments 1-13, further comprising a capillary observation window to view flow of collected blood along the capillary tube.

15. The integrated sample collection device of any embodiments 1-14, further comprising a blood collection observation window to view collection of blood in the blood storage container.

16. The integrated device of any of embodiments 1-15, wherein the stabilizing agent comprises an anticoagulant that coats a lumen wall of the capillary, such as an anticoagulant comprising EDTA.

17. The integrated device of any of embodiments 1-16, wherein the penetrating member comprises a lancet, wherein the lancet is formed of a metal or a plastic.

18. The integrated device of any of embodiments 1-17, wherein the biological fluid sample comprises whole blood.

19. The integrated device of any of embodiments 1-18, wherein the pre-processing agent is one or more of a: cell culture media, a PCR reagent, a label, and/or a binding agent.

20. The integrated device of any of embodiments 1-19, further comprising a container safety in operable communication with the vacuum-assisted blood collection container to prevents unwanted actuation movement of the vacuum-assisted blood collection container toward the capillary tube.

21. The integrated device of any of embodiments 1-20, further comprising a removable capillary cover to cover a distal end of the capillary tube and a removable lancet cover that covers a distal penetrating end of the lancet when the device is not in use.

22. The integrated device of any of embodiments 1-21, configured to receive a user-force against a distal end of the housing and/or proximal end of the housing to actuate a motion of the penetrating member to pierce a skin surface.

23. An integrated sample collection device for self-collection of a blood sample from a user comprising: a housing configured to be held by a user; a contact-activated penetrating member disposed at least partially in the housing and configured to penetrate skin; a capillary tube disposed in the housing and having a distal end configured to collect blood released from the penetrating member that penetrates the skin and an actuatable penetrating proximal end; a vacuum-assisted blood collection container at least partially disposed in the housing and configured to temporarily fluidically connect to the capillary tube to receive at least a portion of the collected blood from the capillary tube upon an actuation force applied to the vacuum-assisted blood collection container; a stabilizing agent for stabilizing collected blood in the capillary tube, the vacuum-assisted blood storage container, or both.

24. The integrated sample collection device of embodiment 23, further comprising a solid phase absorption substrate fluidically connected to the capillary tube.

25. The integrated sample collection device of embodiment 23, further comprising a second vacuum-assisted blood storage container and a second capillary tube to provide two separate blood sample storage containers.

26. The integrated sample collection device of any of embodiments 1-25, wherein each blood storage container is configured to contain between 1 μL and 5000 μL, including between 10 μL and 500 μL, of whole blood and has a container volume of between 10 μL and 5000 μL.

27. The integrated sample collection device of any of embodiments 1-26, further comprising a foot connected to or extending from the housing to provide a device relative to horizontal angle that is greater than or equal to 3 degrees and less than or equal to 30 degrees for a device resting on a horizontal surface with the foot and the housing in physical contact with the horizontal surface.

28. A method of sampling a blood sample, the method comprising the steps of: transporting the blood collection container from any of the devices of embodiments 1-27 to a laboratory for sample processing, wherein the blood collection container contains a blood sample from a user; wherein during the transporting, at least a portion of the sample undergoes one or more pre-processing steps, thereby decreasing sample processing time by the laboratory.

29. The method of embodiment 28, further comprising the step of: self-collecting a plurality of blood samples and storing them in a plurality of blood storage containers and at least one solid phase absorption member.

30. The method of embodiment 29, wherein the self-collecting step comprises: providing the integrated sample collection device to a user providing the blood sample(s); user-contacting with skin so that the penetrating member penetrates the skin; moving the integrated sample collection device so that a distal end of the capillary tube is in fluid contact with blood at the site where the penetrating member penetrated the skin; observing blood collection in the capillary tube; and actuating a proximal end of the capillary tube and/or the collection container to thereby cause penetration of the vacuum-assisted blood storage container and flow of blood from the capillary tube to the blood storage container.

DETAILED DESCRIPTION OF THE INVENTION

Figure 1A:
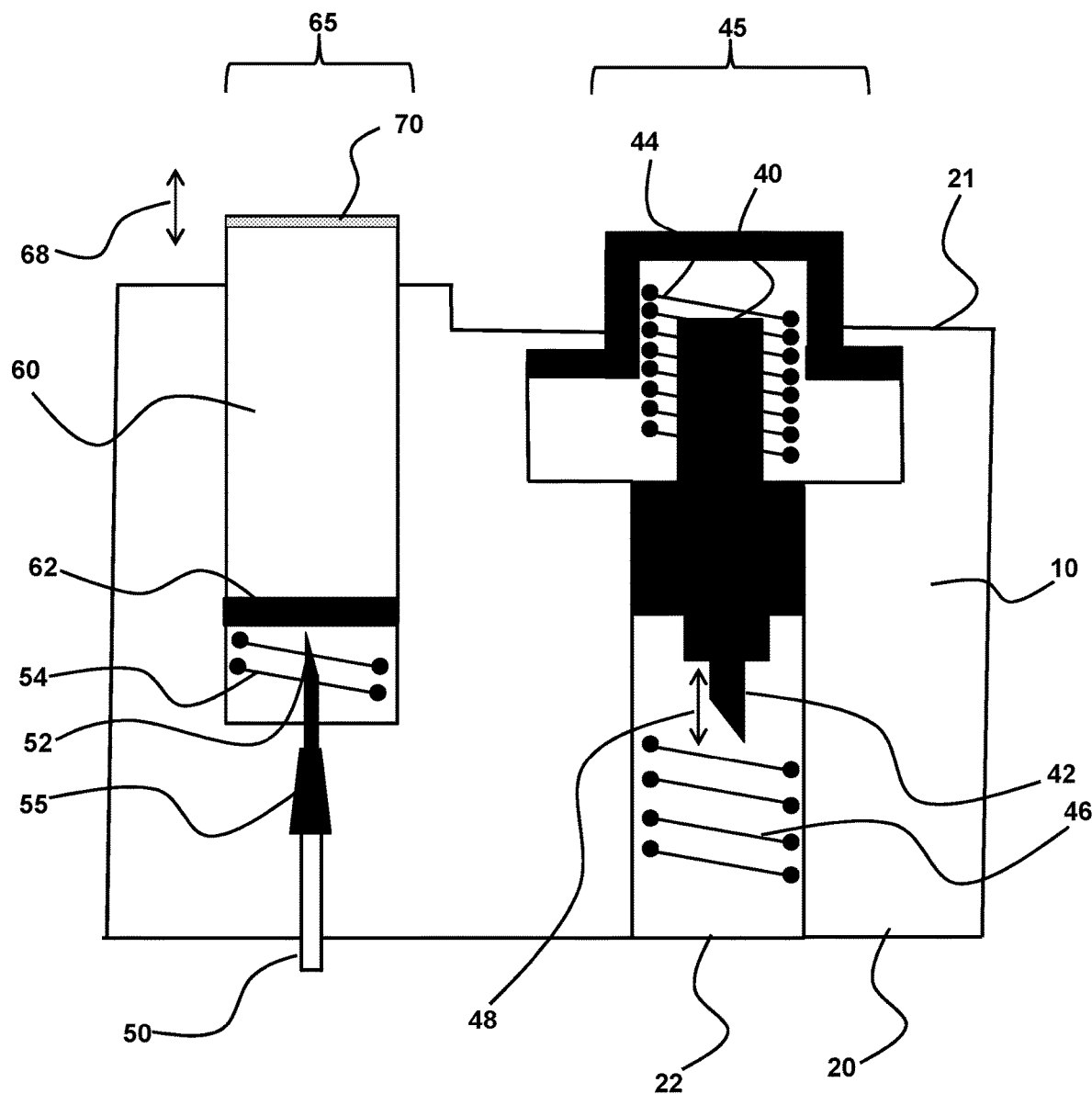
FIG. 1A. An integrated blood collector capable of liquid reagent storage by a VacuStor tube for sample pre-processing.

In general, the terms and phrases used herein have their art-recognized meaning, which can be found by reference to standard texts, journal references and contexts known to those skilled in the art. The following definitions are provided to clarify their specific use in the context of the invention.

The devices and methods provided herein are compatible with a range of biological fluids, and not just blood, whole blood, or constituents thereof. Examples of biological fluids include, but are not limited to, saliva, urine, sweat, cerebral fluid, semen, vaginal fluid, exudate formed at an inflammation (e.g., tissue damage such as a cut or other trauma injury) site, pleural effusions or other liquid biopsy. For the sake of clarity, biological fluids will be preferably described in this disclosure as whole blood, but this invention is compatible with other biological fluids readily processed in medicine. Accordingly, as used herein the term "blood" is interchangeable with the term "biological fluid", including any one or more of the biological fluids described herein.

The vacuum-assisted blood storage container may correspond to a BD Vacutainer® collection tube. The capillary tube may correspond to a plastic blood capillary tube. The lancet may be a safety-lancet Extra 18 G. The special integration of these components into an integrated device, such as contained in a housing, improves integration and self-operation, thereby achieving a stand-alone, self-operated device. Associated and fully integrated consumables, reagents, and/or solid substrates provides for pre-processing and storage of blood, including blood having different volumes as required by a downstream laboratory-based assay. This functionality facilitates subsequent assays and analysis for a range of parameters, including performing the micronuclei cytogenetic test, gene expression and metabolomics profiling from the point of collection, transportation and delivery to the utilization sites where samples can be directly loaded within high-throughput analytical laboratory instrumentation. Similarly, increased integration of the components into a standalone device whose performance will gain from the selective manufacturing of plastic and hybrid polymer materials, more suited for transfer to other large scale production settings of an industrial partner (e.g. injection molding), provides further improvements.

The blood storage container may have any number of agents disposed therein, including prior to or after blood storage in the container, depending on the assay of interest. For example, the agent may be a fluid, such as media and constituents therein for cell culture, amplification (e.g., PCR reagents), a solid substrate or membrane, labels and the like. For example, the membrane may be placed or manually transferred to into a non-vacuum storage container into which the biological sample is introduced. Similarly, the capillary tubes and/or vacustor containers used to collect blood may contain desired agents.

"Fluidically connected" refers to a configuration of elements, wherein a fluid (e.g., liquid, gas or viscoelastic material) in one element is able to enter another element in a manner that does not affect each element's functionality. For example, a vacuum-assisted blood storage container is fluidically connected to the capillary tube such that blood that is in the capillary tube is capable of being provided to the storage container. The term fluidically connected is compatible with one or more intervening components between the elements. For example, a sharp-tip may be positioned between the capillary tube and storage container to pierce the storage container, such as an elastomeric lid, so that the vacuum pressure in the container drives at least a portion of the blood from the capillary tube to the container. Upon removal of the sharp tip from the elastomeric lid, the lid seals, thereby reliably storing blood in the container.

"Held by a user" refers to a device that can be held in a hand so that blood is collected from the user, such as from a fingertip of the other hand.

"Penetrating member" refers to component that is capable of piercing skin and drawing blood that can then be collected by the capillary tube, such as by capillary action.

"Contact activated" refers to a component that is actuated by a physical force. The physical force may be when the device is brought into contact with the skin or may be with a separate component where a physical force is transmitted to the active component, such as a button, switch or the like.

Example 1: Device Characterization

Provided is an integrated skin puncture blood collection device, including for radiation countermeasure for high throughput sample self-collection with liquid reagent pre-processing capability. A key process of the device, i.e. sample transfer from capillary to the vacuum tube, was modeled theoretically and characterized experimentally. Ideal gas law was shown to be a good model for threshold vacuum prediction, and barrier coating and temperature-induced low permeability were shown to extend the shelf life of the vacuum tube over a year. Gene expression levels were detected for all assayed genes using blood sample collected by the system, and were similar to those by conventional procedures.

Introduction: Blood collection and processing are critical steps in the pre-analytical phase of diagnostic testing. Multiple devices and components are usually involved, including a lancet or needle for blood vessel access, a storage container, and a way to transfer blood from blood vessel to the container. So far, most of integrated microfluidic analytical devices focused on implementation of sample-to-answer assay processes. There has been no report on integrated front end blood collection with added liquid reagent sample pre-processing for high throughput central laboratory assays. But it can be critical in certain applications. One example is in the development of high throughput biodosimetry for radiation countermeasure.

In a large scale nuclear/radiation event in a metropolitan area, it is estimated over a million people would seek information on their exposure levels. High throughput biodosimetry is the key in patient triage and management in radiation countermeasure. It requires sample (blood) collection and pre-processing in the field before shipment to central laboratories for analysis. However, current blood collection and pre-processing procedures cannot meet the need of the application as stated by the reasons below:

First, traditional blood collection method, such as venipuncture, could present a great bottleneck due to its requirement of trained medical personnel that may not be available in the chaotic aftermath of a radiological event. Skin puncture blood collection requires less training and may be self-administered, but handling the multiple components in a collection kit can also be error-prone.

Second, liquid reagent sample pre-processing is critical for biodosimetry assays. For gold-standard cytogenetic biodosimetry assays, blood cell culture is time consuming (48~72 hours) and currently it only starts after samples have been shipped to the central laboratory. The shipment itself can take as much as 3 days, depending on the shipping conditions, which can greatly increase the time it takes for the assay results to be available. Pre-stored cell culture medium, however, could allow blood cell culture to start right after collection and during shipment using a shipping incubator to enable disruptive biodosimetry logistics to dramatically cut down the response time. Besides cytogenetic assays, gene expression biodosimetry5 assays also require blood RNA stabilization solution. Manual pipetting is the traditional way of liquid handling, but it is a multiple-step slow process requiring additional tools and supplies that is not suitable for the application. The biological fluid containers of the devices provided herein are configured for use with a wide range of shipping containers, including smart shipping containers.

To address the above mentioned issues, provided herein is an integrated skin puncture blood collector with liquid reagent storage capability to streamline the collection and sample pre-processing processes for possible self-collection. In this example, we will show the design of the integrated blood collector, as well as characterization of a critical subsystem of the collector, i.e. a miniature vacuum tube system.

Integrated blood collector design, prototyping and rationale for VacuStor system characterization:

FIG. 1A is a schematic illustration of an integrated sample collection device 10 for self-collection of a biological fluid, such as blood. The device integrates multiple components into one device that can be held by a single hand of a user 30 (see, e.g., lower right panel of FIG. 1B) for ease of operation and self-collection. It comprises a housing 20, having a proximal end 21 and a distal end 22, that at least partially contains a blood-obtaining assembly 45 to make blood available through the skin and a blood-collecting assembly 65 to collect and contain sampled blood. Distal end refers to the surfaces and positions that are towards a surface that fluid will be collected from. Accordingly, proximal end is away from such a fluid collection point.

The blood-obtaining assembly 45 includes those components that together function for safe and reliable puncture of skin to make blood available. The assembly 45 may include a contact-activated penetrating member 40, such as a penetrating member that is a lancet 42, for skin puncture, and various springs 44 46 to facilitate actuation and retraction of lancet 42. Accordingly, any of the devices provided herein may be described as having an actuated and a retracted configuration with respect to the penetrating member. In an actuation mode, the penetrating member is physically accessible and at least partially positioned external to the housing. In the retracted mode, the penetrating member is physically inaccessible to avoid unwanted or inadvertent contact with shape surface of penetration member. Force springs 44 may facilitate user depression of member 40 that, in turn, forces penetrating end of lancet 42 in a direction out of the housing 20 and into biological tissue adjacent to housing 20. User release causes lancet to retract back safely into the housing, thereby avoiding risk of accidental injury. This force actuated deployment and storage motion is reflected by arrow 48.

Figure 15:
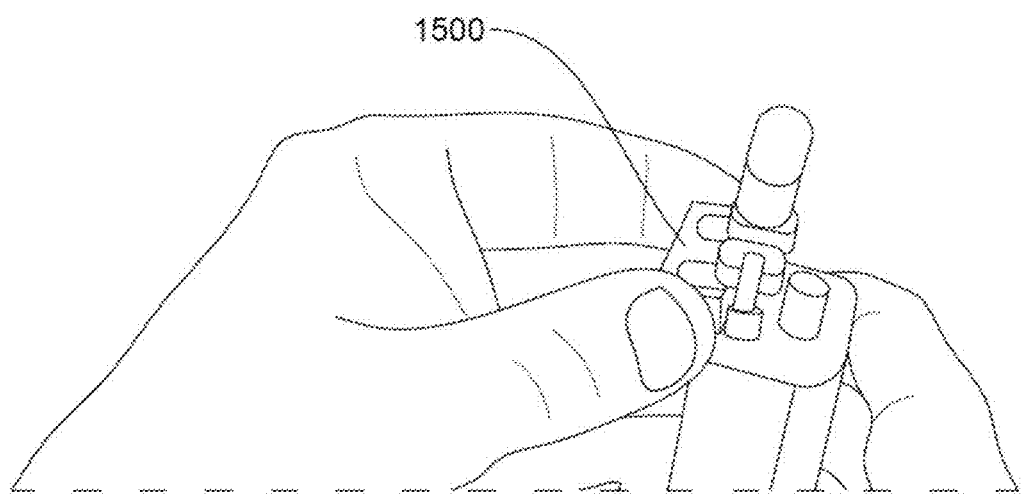
FIG. 15. Remove tube safety and depress tube holder to transfer samples into the collection tubes. The transfer process can be observed via the observation windows and can be extremely fast.
Figure 16:
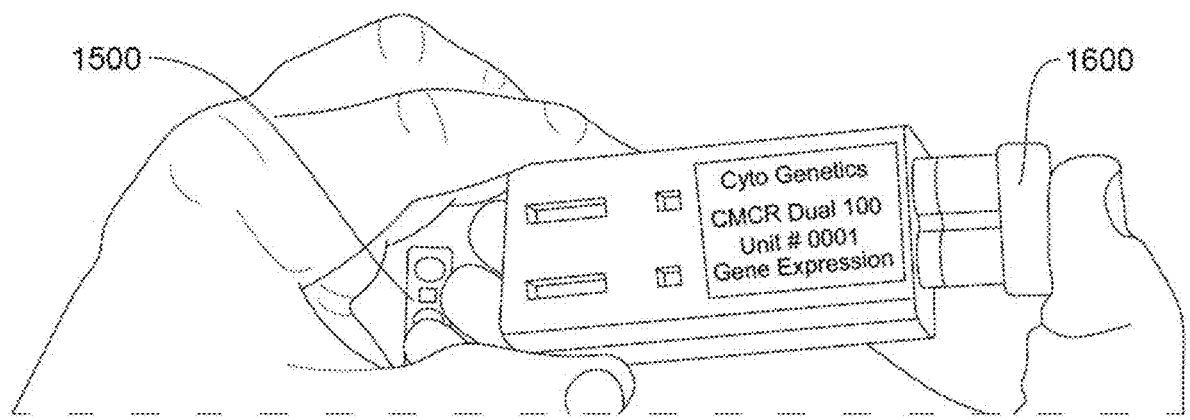
FIG. 16. Initiate sample transfer into collection tubes by removing safety and forcing capillary (including a sharp needle connected to the capillary tube) to penetrate the vacuum container. Blood flow out of capillary into container can be visually observed through windows.
Figure 17A:
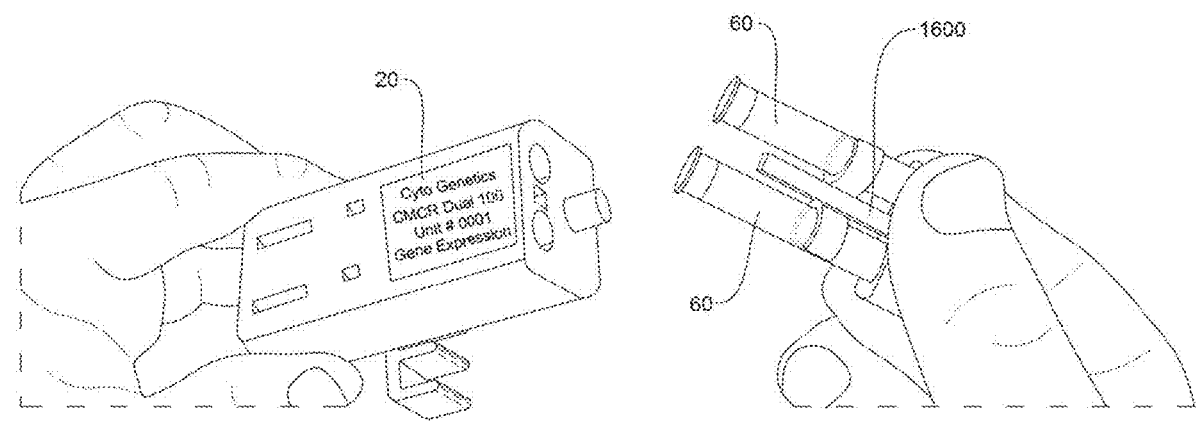
FIG. 17A. Remove tube holder and tubes from blood collector device. Remove each tube and place in corresponding tray color coded. One tube can correspond to a first assay and a second tube to a second assay. For example, green (e.g., top; photo shows blue rubber stopper) for cell culture testing and Lavender (e.g., bottom tube; photo shows yellow rubber stopper) for RNA assay testing.
Figure 17B:
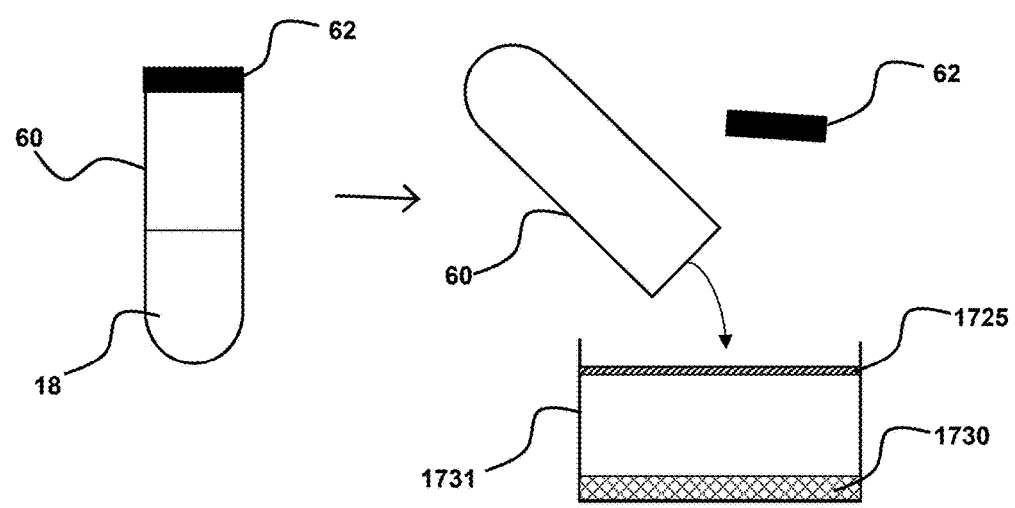
FIG. 17B illustrates fluid sample in collection container, that is subsequently transferred to a storage container, including a storage container having a solid phase absorption member and/or an extraction substrate.

Blood-collecting assembly (also referred to as a capillary-needle assembly) 65 can then reliably collect and contain blood made available by assembly 45. Capillary-needle assembly 65 refers to the collection of components, including within housing 20 that are configured to collect and store fluid sample, and may comprise a capillary tube 50 to collect accessible blood provided by penetrating member 40, penetrating needle 52 (also referred herein as a "transfer needle") and an adapter 55 to reliably and fluidically connect needle 52 to capillary tube 50. Needle 52 is configured to pierce cap 62 of miniature vacuum storage tube 60 and/or capillary tube 50. One or more stabilizing and/or pre-processing agents 70 can be provided in the vacuum assisted blood storage container 60. In this manner, the assembled components of capillary-needle assembly 65 together provide for metered blood collection and cap piercing, with a vacuum-assisted collection container 60 for liquid reagent storage and sample pumping, for subsequent pre-processing and/or shipment. A retainer with spring 54 prevents accidental piercing of the cap 62 and also helps to push the tube 50 back after piercing, as indicated by arrow 68. For self-collection, the collector can be held by one hand to lance the finger from another hand (or other skin area), followed by blood collection from the lanced area using the capillary (see, e.g., FIG. 1B, bottom right panel). Then the blood-collection container(s) 60 can be pushed to pierce the tube cap 62 by the needle (after removal of an optional tube safety lock 1800 (see, e.g., FIGS. 15 and 18) to transfer the blood sample into the tube by vacuum for pre-processing by the liquid reagent 70. Finally, the collection containers 60 can be removed from the device (see, e.g., FIG. 17A) for subsequent processing, transfer to a different storage container (FIG. 17B), and/or for shipment, such as by a holder 1600. Holder 1600 can hold one or more collection containers 60 and is removably insertable into the housing. Holder can be actuated to collect blood by forcing capillary tube, including a piercing needle connected thereto, into the interior volume of the collection container 60; flow is driven via a pressure differential.

Figure 1B:
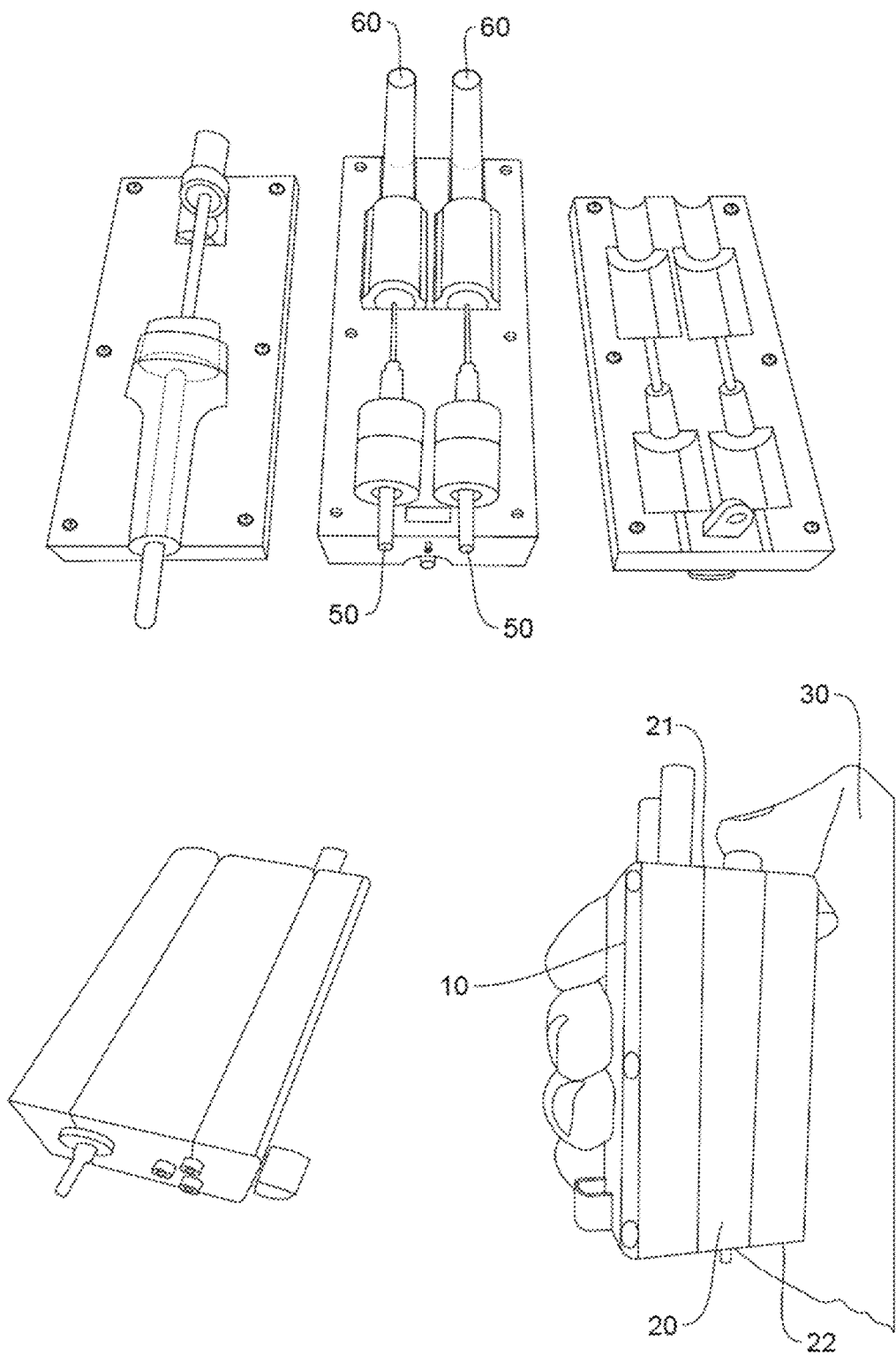
FIG. 1B is a blood collector obtained by 3D printed packaging containing a lancet and two VacuStor systems for multiple assays.
Figure 22:
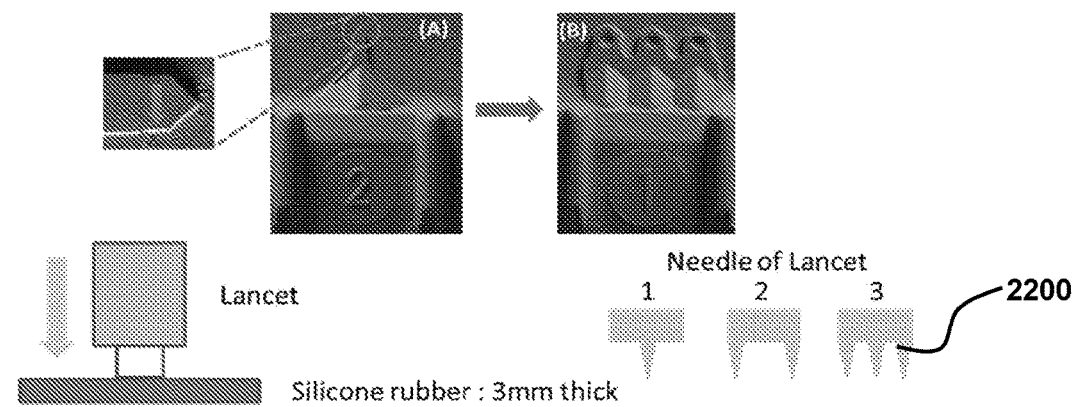
FIG. 22. The top-left panel shows 3D surface mapping of a single needle tip, and higher magnification of the tip including "zig zag" side structures, as reflected by the arrow. The right panel illustrates a three needle lancet configuration, illustrating that any of the devices provided herein are compatible with any number of contact-activated penetrating members, with one, two and three penetrating members illustrated under the "needle of lancet" image. Images are acquired by using gel-based photometric stereo profilometry. The bottom table panel shows test results using the penetration test into silicone-based membrane as a skin equivalent model. Reliable penetration depths are achieved, even for three different penetrating members. As expected, for a given force, as the number of penetrating members increase, the penetration depth decreases, so that the contact-activated force may be correspondingly increased as the number of penetrating members increase to achieve a desired penetration depth and ensure appropriate blood release to, for example, finger-tips.

FIG. 1B shows a device fabricated by 3D printed envelopes to package together a commercial lancet, capillary-needle assemblies, and VacuStor tubes made from commercial miniature storage tubes in a 96-tube-rack that are compatible for automated laboratory analysis. We call one capillary-needle assembly and one VacuStor tube together as a VacuStor system. Two VacuStor systems are integrated to show the possibility of the collector for multiple assays by a plurality of capillary tubes 70 and collection containers 60. A commercial lancet is used for quick evaluation of the concept. Novel lancets can also be used for improved benefits if needed. For a commercial lancet, the skin puncture can follow the standard procedure specified by the manufacturer. As desired, multiple lancets (e.g., FIG. 22, showing 1-3 lancet configurations) can be used for a one-step multiple piercing of skin at a plurality of distinct locations. A relevant aspect of the device lies in the VacuStor system to successfully transfer blood sample from the capillary to the VacuStor tube containing liquid reagent, with reliable removal of one or more storage tubes for subsequent processing and/or shipping.

Integrated liquid reagent storage has been reported for integrated microfluidic devices using glass ampoules, pouches/blisters and stick packs with external pressure pumps for further fluid movement. The vacuum tube is a more convenient system because vacuum can act as a built-in pump. Vacuum tubes have been used for blood collection and demonstrate significant improvements in collection safety, speed and sample integrity. They also have liquid storage capability that is difficult to integrate in other blood collection methods. However, current vacuum tube systems are mainly designed for venipuncture with large tube size, and are not suitable for high throughput bioassays. Recently, there was a report of a vacuumed PDMS mini-chamber with a microfabricated hollow needle for small volume blood collection from a rabbit ear artery. However, the storage lifetime of the mini-chamber can be a concern due to vacuum loss from the high surface-to-volume ratio. Even though gas permeation of materials has been characterized and vacuum tubes have been used in clinical practice, no theoretical model has been published regarding the design of air evacuation for blood collection except some empirical observations, such as how blood draw volume varies with altitude. To fill this knowledge gap, we characterize the sample transfer and shelf life of the VacuStor system. We also demonstrate the utility of the VacuStor system for gene expression assay to show the potential of the system for high throughput biodosimetry assays for radiation countermeasures.

Figure 2A:
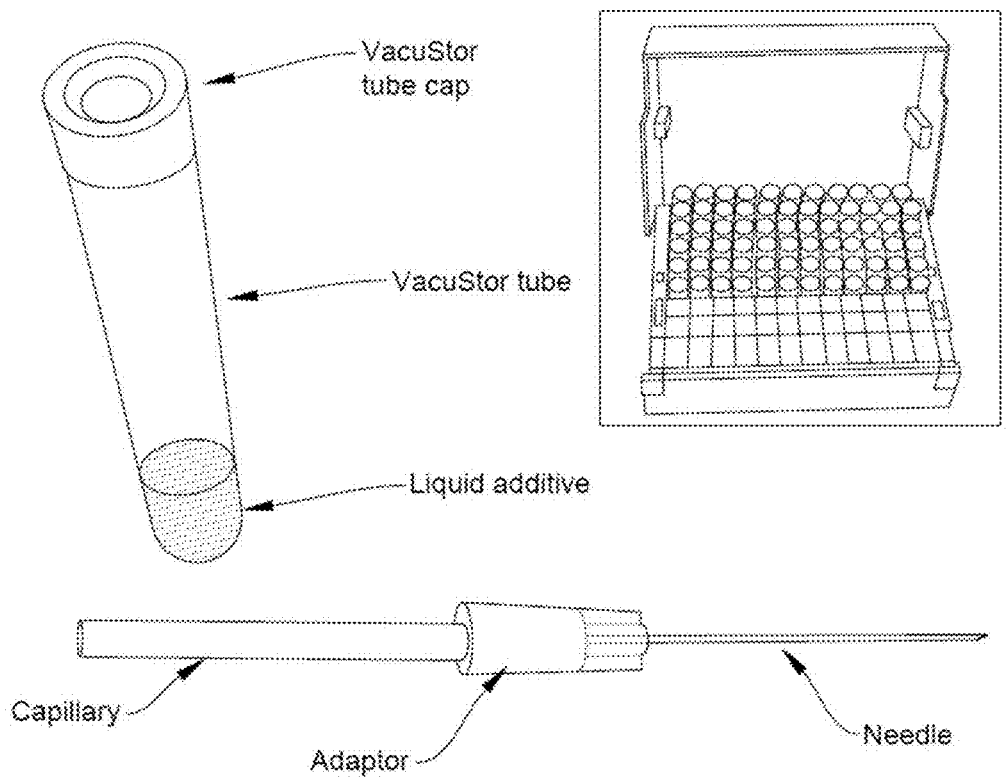
FIG. 2A. Image of a VacuStor tube and a capillary-needle assembly. The insert shows an opened 96-tube rack.

Results and discussion: FIG. 2A shows a picture of a nominal 1.0 ml glass VacuStor tube, cap and a capillary-needle assembly used in this study. The detailed fabrication process is listed in the Experimental section.

There are two parameters that are important to the functionality and practical use of the VacuStor system. The first is a threshold tube vacuum pressure ($P_{th}$), below which all the blood can be transferred from the capillary into the tube. The second is the shelf life ($T_{sh}$) of the tube due to vacuum loss. We use the ideal gas law and gas permeation theory to characterize the two parameters.

Figure 2B:
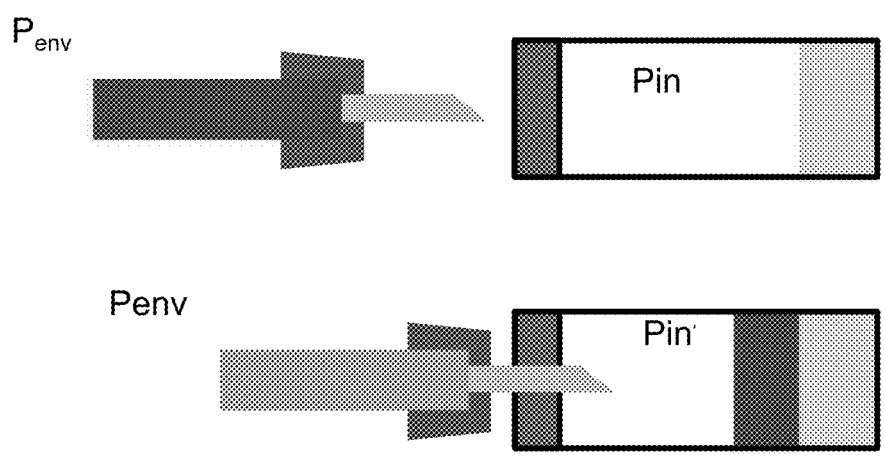
FIG. 2B Schematics of VacuStor tube system before (top panel) and immediately after (bottom panel) transfer of all the blood from the capillary tube to the container.

Threshold vacuum pressure ($P_{th}$): FIG. 2B shows schematics of a VacuStor tube system before and immediately after transfer of all the blood from the capillary into the tube, with $P_{in}$ and $P_{in}'$ as the respective tube pressures and $P_{env}$ as the environmental pressure. To have a proper sample transfer, in a capillary tube open to the environment, we have:

$$P_{in}' \leq P_{env} \quad (1)$$

At standard temperature and pressure where most blood collections are conducted, ideal gas is a good approximation for air. According to the ideal gas law, we have:

$$P_{in}' = \frac{V_t - V_a}{V_t - V_a - V_b} * P_{in} \quad (2)$$

where $V_t$, $V_a$ and $V_b$ are the tube, additive and blood volumes respectively. From Eq. (1) and (2), we have:

$$P_{th} = \frac{V_t - V_a - V_b}{V_t - V_a} * P_{env} \quad (3)$$

Saturated water pressure at room temperature from aqueous reagent and needle capillary pressure are a few kPa or less, on the same order as the accuracy of the pressure gauge we used (±3% of 100 kPa), and are neglected here.

Figure 3:
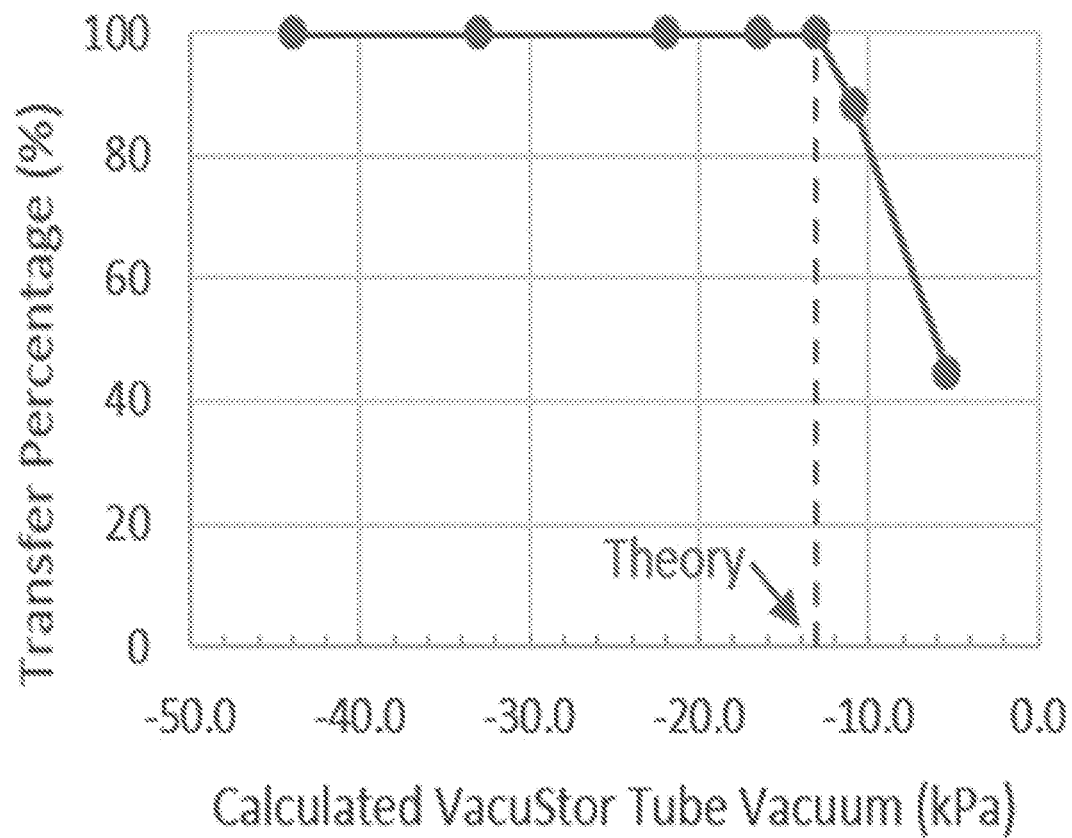
FIG. 3. Dots: experimental results of sample transfer percentage vs. calculated VacuStor tube vacuum; dashed line: threshold vacuum prediction by Eq. (3).

FIG. 3 shows the experimental results of how the sample transfer percentage depends on the VacuStor tube vacuum for an additive volume of 300 µl and sample volume of 100 µl (blue dots). The threshold vacuum was measured to be −13.1 kPa relative to the environmental pressure. The calculated threshold vacuum by Eq. (3) was 13.0 kPa (vertical dashed line), indicating a good model of ideal gas approximation. (See Experimental for detailed experimental and theoretical calculations.)

One requirement on the needle selection for the sample transfer process found during the experiments is that the depth of the needle bevel should be shorter than the thickness of the rubber cap. If the bevel depth is longer than the cap thickness, it will bridge the tube inner and outer spaces to cause a vacuum leak, which will cause a failure in transfer. The thickness of the tube cap is measured to be 1.2 mm, which limits the needle gauge to be 27 or higher for a typical 12° bevel.

Shelf life ($T_{sh}$): Shelf life ($T_{sh}$) of the VacuStor tube due to vacuum loss is related to the pressure increase from gas permeation of the rubber cap (the glass tube used in this study is considered non-gas-permeable). We approximate the gas permeation by Fick's first law[13]:

$$j = \frac{D(C_{env} - C_{in})}{\delta} = \frac{DS(P_{env} - P_{in})}{\delta} = \frac{P_e(P_{env} - P_{in})}{\delta} \quad (4)$$

where j is the flux density, D is the diffusion coefficient, $C_{env}$ and $C_{in}$ are the gas concentrations of the environment and inside the tube respectively, $\delta$ is the cap thickness, $P_{env}$ and $P_{in}$ are the respective pressures, S=C/P is the sorption equilibrium parameter, and $P_e$=S*D is the permeability. Then the mass transfer flux rate:

$$I = j*A = P_e*(P_{env} - P_{in})*A/\delta \quad (5)$$

where A is the area of the cap. From the ideal gas law, we also have:

$$I = \frac{dN}{dt} = \frac{V}{RT} \frac{dP_{in}}{dt} \quad (6)$$

where N is the amount of gas in moles, V is the tube volume, R is the gas constant and T is the absolute temperature. From Eq. (5) and (6), the internal gas pressure change over time can be deduced as:

$$\Delta P(t) = \Delta P(0) * e^{-\frac{t}{t_{lk}}}, \text{ or } \Delta P'(t) = -\frac{\Delta P(t)}{\Delta P(0)} = -e^{-\frac{t}{t_{lk}}} \quad (7)$$

where $t_{lk}=(V*\delta)/(P_e*A*RT)$ is the leaking time constant, $\Delta P(t)=P_{in}(t)-P_{env}$, $\Delta P(0)=P_{in}(0)-P_{env}$, and $\Delta P'(t)$ is the normalized vacuum pressure (the negative sign is to show the pressure is below the environmental pressure).

One thing to be noticed is that air is a mixture of multiple gases that their permeability for the rubber cap can be different. With the ideal gas approximation, all the gas molecules interact with each other only through elastic collisions, and each gas can be treated independently. For the tube pressure increase through permeation, we will consider only the two most abundant gases in the air, i.e. nitrogen (78%) and oxygen (21%), and the remaining 1% (mainly argon) will be treated as 0.5% of nitrogen and 0.5% of oxygen to simplify the situation. If we assume nitrogen and oxygen are pumped out of the tube at the same rate so that they have the same percentage in the evacuated tube at time zero as in the air, then the total normalized vacuum pressure:

$$\Delta P'(t) = -\frac{\Delta P_n(t)}{\Delta P(0)} - \frac{\Delta P_o(t)}{\Delta P(0)} = -0.785 * e^{-\frac{t}{t_n}} - 0.215 * e^{-\frac{t}{t_o}} \quad (8)$$

where $t_n = \frac{V*\delta}{P_{e,n}*A*RT}$ and $t_o = \frac{V*\delta}{P_{e,o}*A*RT}$.

Figure 4:
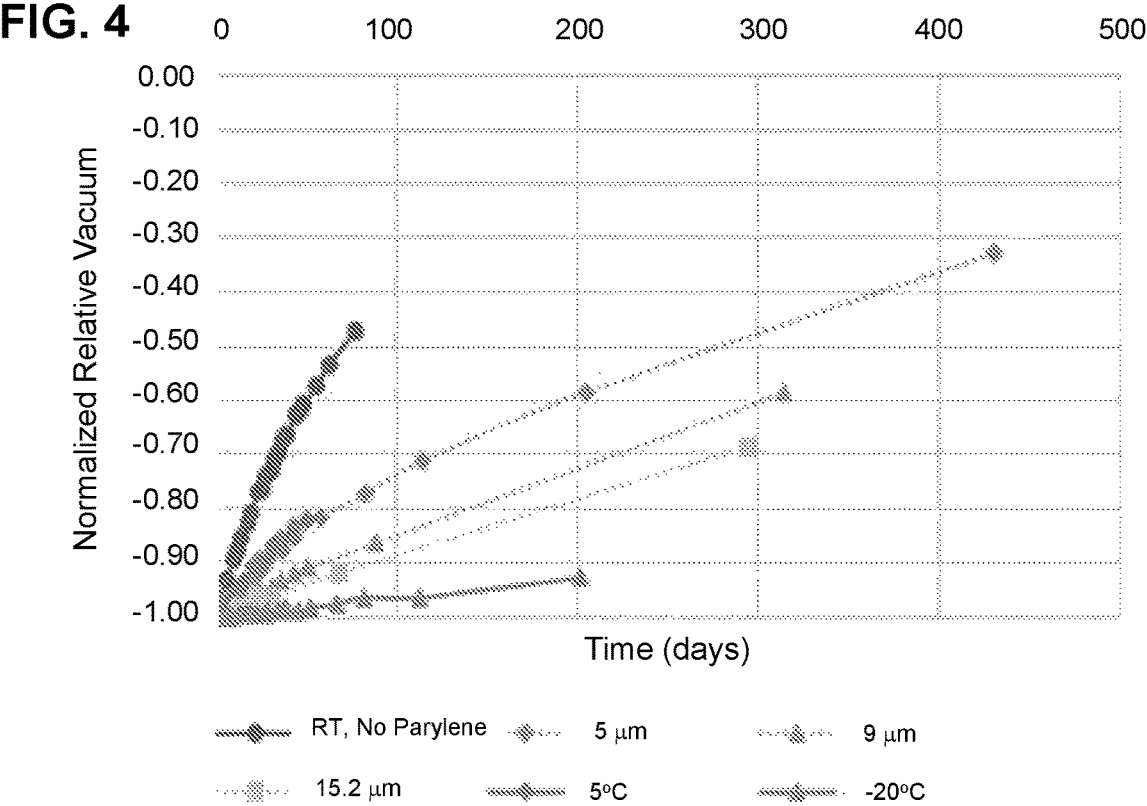
FIG. 4. Change of normalized pressures over time for VacuStor tubes under different conditions (performance of one tube out of three replicates was plotted for each condition).

By drilling a hole at the bottom of the VacuStor tube, and gluing it to a vacuum gauge, the normalized vacuum pressures over time under multiple conditions are measured experimentally, as shown in FIG. 4. Because the vacuum gauge has an internal volume $V_{gauge}$ of 1.45 mL that will increase the time constants, we denote the measured time constants as $t_n'$ and $t_o'$. It can be seen in FIG. 4 that for a VacuStor tube at room temperature without any coating, the vacuum dropped to 47% in 77 days. By fitting the result using Eq. (8) using Excel (from Microsoft), $t_n'$ and $t_o'$ were found to be 134.4 and 40.3 days respectively. The real $t_n$ and $t_o$ of the tube were calculated as 56.2 and 16.8 days. Assuming an initial vacuum ΔP(0) of −85 kPa and a threshold vacuum of −20 kPa, the shelf life of the VacuStor tube due to gas leakage was calculated by Eq. (8) to be 67 days, too short to make the device commercially feasible.

For a practical shelf life of VacuStor tubes (e.g. 365 days), we consider the scaling law of the gas leaking time constant $t_{lk}$, which is on the same order of the shelf life. Eq. (7) shows that $t_{lk}$ is proportional to V and δ, and inversely proportional to $P_e$, A and T. Because the miniaturization of tube usually leads to increased surface to volume ratio (A/V) and smaller cap thickness δ, the shelf life of VacuStor tube can be much shorter than that of larger evacuated tubes. To increase $t_{lk}$, $P_e$ and T need to be reduced. Reduction of T is usually limited to only ~20%, but lower T can dramatically reduce the permeability of the thermoplastic elastomer cap of the VacuStor tube due to the exponential Arrhenius rule's[15, 16]. If T cannot be lowered, another common way to reduce gas leakage is by adding low permeable barrier coatings (such as Parylene polymer conformal coating[17]). With a two-layered cap, Eq. (4) can become:

$$\left(\frac{\delta_1}{P_{e,1}} + \frac{\delta_2}{P_{e,2}}\right)*j = P_{env} - P_{in} \quad (9)$$

and the new time constant in Eq. (7) will be the sum of the individual time constant, i.e.

$$t_{lk} = t_{lk,1} + t_{lk,2} = \frac{V*\delta_1}{P_{e,1}*A*RT} + \frac{V*\delta_2}{P_{e,2}*A*RT} \quad (10)$$

FIG. 4 also shows how the normalized vacuum pressures changed for VacuStor tubes with 5, 9, 15.2 μm Parylene coating and stored at room temperature, as well as no Parylene coating but stored at 5° C. and −20° C. It can be seen that, indeed, additional polymer coatings reduce the gas leakage significantly; refrigerator temperature (5° C.) also reduced the gas leakage, similar to a 5 μm Parylene coating; freezer temperature (−20° C.) lowered gas leakage the most, presumably through the much reduced permeability at low temperature.

Figure 5:
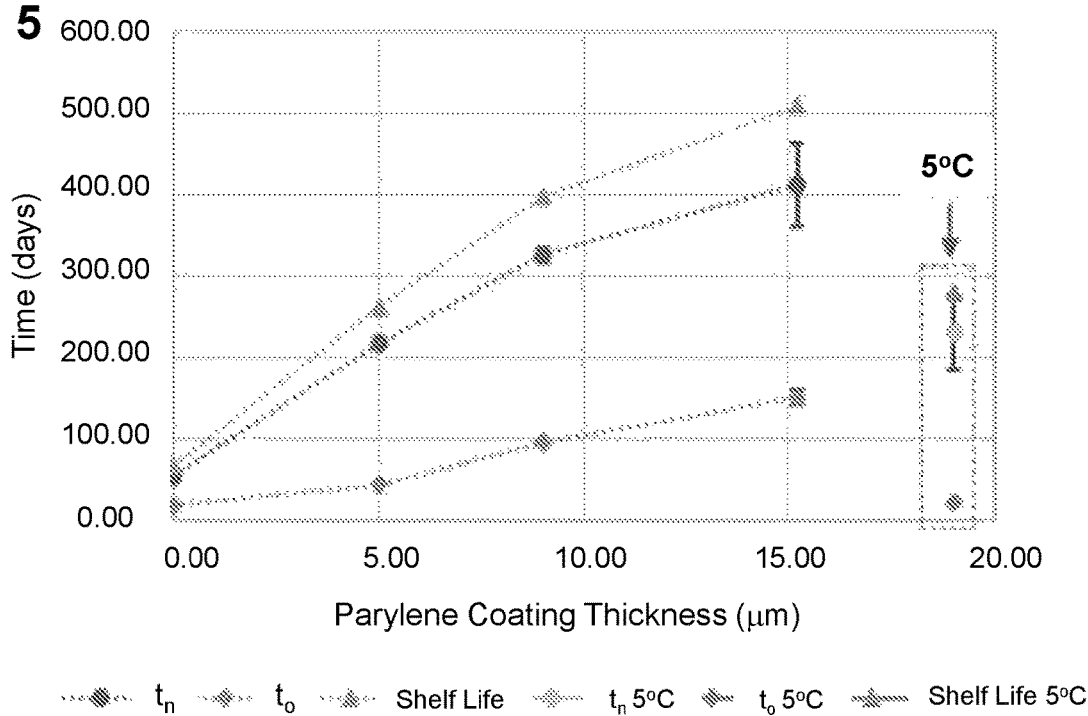
FIG. 5. Means and standard deviations of nitrogen ($t_n$), oxygen ($t_o$) leaking time constants for different Parylene coating thicknesses; the values for 5° C. were also plotted for comparison. Three tubes were analyzed for each condition. Shelf lives were calculated using the mean values.

FIG. 5 shows the mean values and standard deviations of fitted nitrogen, oxygen leaking time constants for three tubes at each condition for different Parylene polymer thicknesses. The variation is larger for thicker coatings because of the smaller vacuum loss within the experimental time frame due to reduced permeability. The time constants also increase linearly with polymer thickness except for $t_n$ at 15.2 μm. This is consistent with Eq. (10); and the reduction of the $t_n$ at 15.2 μm could come from degraded cap sealing due to stress from the thicker polymer. The $t_n$, $t_o$ for 5° C. without Parylene coating were also plotted in FIG. 5 for comparison. For −20° C., we cannot fit $t_n$ and $t_o$ reliably because the limited vacuum loss due to extremely slow gas leakage and an interruption of the experiment at day 202, but is estimated to be several times longer than that of a 15.2 μm Parylene coating. It should also be noted that because oxygen and other gases (except Nitrogen) occupy only 22% of air, the threshold vacuum would not be reached even if they reached equilibrium with the environment. That means the shelf life of VacuStor will only be determined by the leakage of the nitrogen gas, i.e. $t_n$. In FIG. 5, the shelf lives for different conditions were calculated and plotted using mean values of $t_n$, $t_o$ and the previously assumed initial and threshold vacuums. The shelf life shows a linear increase with Parylene thickness with a reduction at 15.2 μm, similar to the trend of $t_n$, but not $t_o$ which shows a linear increase for all Parylene thicknesses, consistent with our analysis. It should also be noted that a 9 μm Parylene coating has an expected shelf life of 389 days, long enough for practical applications.

Figure 6:
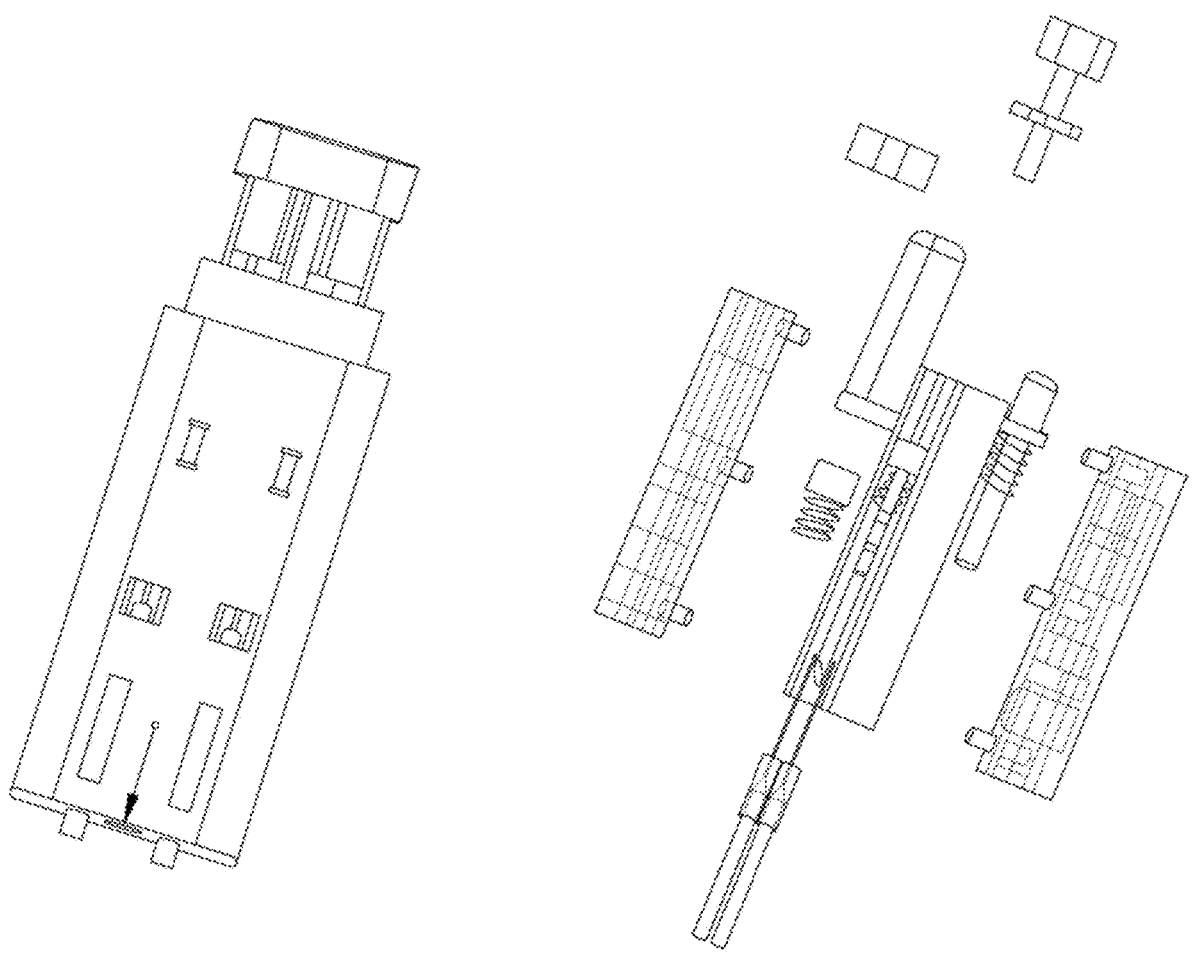
FIG. 6. NUCLEAIR integrated device (left panel) and exploded view (right panel) to illustrate various components.

Finally, to show the utility of the VacuStor system for bioanalysis, we used it to collect blood samples irradiated with either 0 or 5 Gray (Gy) of X-ray for gene-expression analysis using a non-enzymatic chemical ligation process (DxDirect, from Dxterity Diagnostics, CA), and compared the performance with benchtop blood handling by pipetting. Purchased blood was used for convenience. FIG. 6 shows the results of 5 Gy gene expression level normalized by 0 Gy for 5 radiation dose-sensitive genes reported in the literature[5]. Gene expression levels were detected for all 5 genes, and showed trends similar to those of measurements by a benchtop pipetting process, indicating that it can be used for gene expression analysis. Additional experiments will be conducted to statistically validate the system.

Experimental: Integrated blood collector prototyping: Geometries of a fingerprick lancet (Extra Safety-Lancet from Sarstedt Inc. Newton, NC), two capillary-needle assembly and two glass VacuStor tubes were measured. The fabrication of the capillary-needle assembly and VacuStor tube is listed in the next section. 3 envelope layers were printed by an uPrint SE Plus 3D printer (Stratasys, MN) to enclose the components inside one device. An extension rod was used for lancet triggering.

Fabrication of capillary-needle assembly and VacuStor tube: The 100 μL plastic blood collecting capillary from the Microvette 100 collection tube (Sarstedt Inc; Newton, NC) is used in our assembly. The 27 G 1.5" long hyperdermic needle is purchased from EXEUNT International Medical Products. The cannula of the needle is removed from the hub and ground to the appropriate length. Both the capillary and needle cannula were UV glued to an adaptor to complete the capillary-needle assembly. The adaptor is 3D printed using a Form2 SLA printer from Formlabs. After final assembly the needle cannula was cleaned with a sterile cotton swab and isopropyl alcohol.

Matrix 2D barcoded 1 mL open top glass storage tubes from ThermoFisher Scientific Inc. (Item #3850) were used for making VacuStor tubes. The caps are the SepraSeal caps from the same company (Item #4464YEL). A vacuum fixture with a gauge and a feedthrough was built to form the VacuStor tubes with desired level of vacuum.

Threshold vacuum testing: 300 µL of phosphate buffer saline solution (PBS) is pipetted into an empty Matrix tube, and a SepraSeal cap is used to cap the tube. A VacuStor tube with the desired level of vacuum is then produced by adjusting the vacuum according to the vacuum gauge of the vacuum fixture. The vacuum gauge, which measures the pressure difference between the vacuum and the environment, is from SMC Corporation (model GZ43-K-01). The environmental pressure ($P_{env}$) of our laboratory is measured by a digital barometer (VWR, Cat #10510-922) to be 96.8 kPa.

The real tube volume after capping ($V_t$) was measured to be 1042 µl by pipetting 1 ml of PBS and measuring the remaining space dimensions by ruler. During SepraSeal capping, the rubber cap seals the tube at the very top, then comes down further to the final position. There is a tube volume reduction ($V_c$) caused by the process that can raise the tube pressure. $V_c$ was estimated as 77 µl by the geometry of the cap, which is used to correct the tube vacuum by the ideal gas law, $$\text{i.e. } P_{in} = \frac{V_t + V_c}{V_t} * P_{vg},$$

where $P_{vg}$ is the pressure of the vacuum gauge. To be consistent, $P_{in}$ is expressed as the pressure reduction relative to $P_{env}$ in FIG. 2B, and the theoretical threshold vacuum for 300 µL liquid additive and 100 µL sample is calculated as −13.0 kPa using the measured $P_{env}$ value.

To test the experimental threshold vacuum, VacuStor tubes are formed with vacuum gauge readings of −49, −39, −29, −24, −21, −19 and −14 kPa, which correspond to tube vacuums of −44, −33, −22, −16.4, −13.1, −10.9 and −5.4 kPa. The fabricated capillary-needle assembly is used to pick up 100 µL of dyed PBS, then pierce the rubber cap of the VacuStor tube at a horizontal position to transfer the sample to the tube. The transfer time depended on the tube vacuum and was the longest (~10 sec) when the tube vacuum pressure is around the threshold vacuum pressure. The percentage of the sample transfer is measured by the ratio of emptied capillary length to the total capillary length (measured as 35 mm). Three experiments are conducted for each vacuum point. The full transfer is achieved for all vacuum points except −10.9 and −5.4 kPa, where the emptied capillary length is measured to be (33, 30, 30) mm and (15, 15, 17) mm respectively.

Vacuum shelf life: To characterize the vacuum shelf life of the VacuStor tubes, a hole is drilled in the bottom of the glass tube by sand blasting, then the tube bottom was glued to the SMC vacuum gauge using a low outgassing epoxy glue (Torr Seal from Variant Inc). Another vacuum fixture is built to cap the tube under vacuum. Then the vacuum of the VacuStor-gauge assembly is read out over time from the gauge. For low temperature experiments, once the VacuStor-gauge assembly was formed and put into the desired environment, the assembly is allowed to stabilize first before data collection. For Parylene polymer coated caps, 5, 9 or 15.2 µm of Parylene-C coating was coated on the SepraSeal caps by a SCS Labcoater® 2 machine (Specialty Coating Systems, Indianapolis, IN) to form the VacuStor-gauge assembly and monitored at room temperature. The leaking time constants of the VacuStor-gauge assembly ($t_n'$ and $t_o'$) are fitted by the least squares method using GRG Nonlinear Solver from Excel. Because the vacuum gauge has an internal volume Vgauge that is connected with the tube, the real tube time constants $t_n$ and $t_o$ are converted from $t_n'$ and $t_o'$ using equation $t_i = t_i' * V_t / (V_t + V_{gauge})$ where i=n, o. $V_{gauge}$ is measured to be 1450 µL by gluing a syringe to a gauge, then pulling the syringe to a certain volume and calculating $V_{gauge}$ using the ideal gas law from the syringe volume and the vacuum readings from the gauge. After getting $t_n$ and $t_o$, shelf life can be found numerically using Eq. (8) and the initial and threshold vacuums.

Gene expression radiation assay: Human blood was purchased from BioChemed Services (Winchester, VA), mixed with RPMI/10% fetal bovine serum/1% penicillin-streptomycin (blood:media=1:1), and cultured in two 6-well plates in a $CO_2$ incubator at 37° C. for 3-4 hours before irradiation. Irradiation was performed using a cabinet X-ray machine (X-RAD 320, Precision X-Ray Inc., North Branford, CT) at 320 kVp and 12.5 mA with a 2 mm Al filter. The source-to-axis distance was 42 cm. The beam was calibrated using a UNIDOS E PTW T10010 electrometer and TW30010-1 ion chamber, with measurement done in air, for a 15 cm×15 cm field size. A total dose of 0 or 5.0 Gy was delivered to the 6-well plates at a dose-rate of 3 Gy/min. The samples were then cultured at 37° C. for another 24 hours.

A commercially available assay chemistry test (DxDirect, DxTerity Diagnostics, Rancho Dominguez, CA) is used for multiplex gene expression analysis that combines a robust chemical ligation process and a sample stabilization buffer solution (available at http://dxterity.com/dx_direct.php). 100 µL of sample is collected from the 6-well plates using the capillary-needle assembly and transferred into VacuStor tubes containing 200 µL of DxCollect stabilization buffer. For benchtop controls, 100 µL of diluted blood were directly pipetted into micro-centrifuge tubes containing 200 µL of DxCollect stabilization buffer. Samples are immediately stored at −20° C. until analysis. Three independent biological replicates are processed for each condition. The analysis followed manufacture suggested protocols. The final nucleic acid products are analyzed by capillary electrophoresis using ABI 3130xl genetic analyzer from ThermoFisher Scientific Inc. Each nucleic acid product is assayed in duplicate.

For data analysis, fluorescence values of peak height representing each gene are first log-transformed with a base of 2. Gene expression levels are then normalized by the non-radiation-responsive genes MRPS5, MRPS18, and CDR2, as specified in the assay kit, followed by the normalization of 5 Gy gene expression levels by the 0 Gy levels. Analyses are performed with GraphPad Prism version 7.00 for Windows (GraphPad Software Inc., La Jolla, CA).

Provided is an integrated skin puncture blood collector with liquid reagent storage capability for high throughput sample collection and pre-processing for radiation countermeasure. A novel process of the device, i.e. sample transfer from capillary to a miniature vacuum tube, has been characterized and a methodology for analysing evacuated tubes for blood collection has been developed. We have shown that the threshold vacuum of the VacuStor tube can be deduced by ideal gas approximation. Through Fick's law, a scaling law of VacuStor tube shelf life was deduced. And the short shelf life of the VacuStor tube was extended to be over a year by either barrier coatings or low cap permeability at low temperature. Further validation of the VacuStor system and the whole blood collector for different bioassays (e.g. cytogenetics, gene expression) is also underway. Besides radiation countermeasure, the device can be used for other applications where blood can be self-collected by individuals (e.g. at home or in a disaster theater) with liquid reagent pre-processing and sent to a central laboratory for molecular analysis. The vacuum tube methodology developed here can guide the development of other vacuum actuated microdevices References from Example 1

1. R. A. R. Bowen, G. L. Hortin, G. Csako, O. H. Otanez, and A. T. Remaley, Clin. Biochem., 2010, 43, 4.
2. V. Bush, L. Leonard, and D. Szamosi, Lab. Med., 1998, 29, 616.
3. H. M. Swartz, A. B. Flood, R. M. Gougelet, M. E. Rea, R. J. Nicolalde, and B. B. Williams, Health Phys., 2010, 98, 95.
4. Cytogenetic Dosimetry: Applications in Preparedness for and Response to Radiation Emergencies, 2011, INTERNATIONAL ATOMIC ENERGY AGENCY, Vienna.
5. S. Paul and S. A. Amundson, International Journal of Radiation Oncology Biology Physics, 2008, 71, 1236.
6. V. Chai, A. Vassilakos, Y. Lee, J. Wright, and A. Young, J. Clin. Lab. Anal., 2005, 19, 182.
7. J. Hoffmann, D. Mark, S. Lutz, R. Zengerle, and F. von Stetten, Lab Chip, 2010, 10, 1480.
8. D. Chen, M. Mauk, X. Qiu, C. Liu, J. Kim, S. Ramprasad, S. Ongagna, W. R. Abrams, D. Malamud, P. L. A. M. Corstjens, and H. H. Bau, Biomed. Microdevices, 2010, 12, 705.
9. D. Czurratis, Y. Beyl, A. Grimm, T. Brettschneider, S. Zinober, F. Laermer, and R. Zengerle, Lab Chip, 2015, 15, 2887.
10. T. van Oordt, Y. Barb, J. Smetana, R. Zengerle, and F. von Stetten, Lab Chip, 2013, 13, 2888.
11. V. Bush and R. Cohen, Lab. Med., 2003, 34, 304.
12. C. G. Li, M. Dangol, C. Y. Lee, M. Jang, and H. Jung, Lab Chip, 2015, 15, 382.
13. G. VANAMERONGEN, J. Appl. Phys., 1946, 17, 972.
14. M. J. MacNutt and A. W. Sheet, High Alt. Med. Biol., 2008, 9, 235.
15. K. Matsunaga, K. Sato, M. Tajima, and Y. Yoshida, Polym. J., 2005, 37, 413.
16. T. Komatsuka and K. Nagai, Polym. J., 2009, 41, 455.
17. S. Sawano, K. Naka, A. Werber, H. Zappe, and S. Konishi, Mems 2008: 21st Ieee International Conference on Micro Electro Mechanical Systems, Technical Digest, 2008, 419.
18. L. Xu, H. Lee, D. Jetta, and K. W. Oh, Lab Chip, 2015, 15, 3962.

Example 2: Device Characterization

Provided is a medical device for collection, stabilization, and preparation of whole blood during transportation to laboratory facilities equipped for hematology and RNA assay testing. The NUCLEAIR (Numerous Capillaries Lancet Emergency Assays for In-Route processing) device is a point-of-contact system for the self-collection of multiple blood sample volumes (by trained healthcare worker or untrained layperson) from a finger-stick.

The NUCLEAIR device is designed as an "integrated sample collection device" for multiple blood specimen volumes. By integrating the self-collection of blood drops from a finger-stick using a lancet with multiple needles onto (1) a solid absorptive/extraction substrate (fabric or paper), (2) into two capillaries of controlled volumes and using both manual transfer into a storage tube (solid absorptive substrate) and vacuum needle actuation for transferring the liquid blood into two tubes filled with reagents for stabilizing or preparing cell culture of the specimen(s). We provide an integrated collection device for multiple sample volumes and a method for storage and shipment to external laboratories equipped for hematology and RNA assay testing. The integrated medical device includes the following: 1) manual surgical instrument for general use (e.g. lancet), 2) capillary blood collection tubes, 3) vacuum-assisted blood transfer system, 4) empty storage tube and 5) various reagents to stabilize, prevent coagulation or initiate cell culture. This integrated device need not include the laboratory assay, but provides for the stabilization and transport of the whole blood specimens to the laboratory during the blood collection step.

The NUCLEAIR integrated device is can be used as an "integrated sample collection device" for multiple blood specimen volumes by a trained healthcare worker or an untrained layperson.

Self-collection of blood drops from a finger-stick using (1) a contact-activated lancet with multiple plastic needles, (2) a solid absorptive extraction substrate (fabric or paper), (3) two capillaries to control sample volume is further integrated by providing methods to transfer the collected samples into storage tubes that contain reagents for stabilization and assay preparation during transit to laboratories equipped to perform hematology, cell culture and RNA assay tests. The integrated transfer methods are achieved by user actuation to transfer the liquid blood using vacuum assisted transfer and instructions for use to place the solid phase absorption substrate into a storage tube with cap. Here we provide an integrated collection device for multiple sample volumes and a method for storage, stabilization, pre-processing and shipment to external laboratories equipped for testing. The NUCLEAIR collector system (integrated device) includes the following components: 1) manual surgical instrument for general use (e.g. lancet), 2) capillary blood collection tubes, 3) vacuum-assisted blood transfer system, 4) storage tube(s), 5) Reagents to stabilize whole blood and 6) a solid phase extraction substrate.

The integrated device includes the following components:
1) Manual surgical instrument for general use (e.g. lancet)
2) Capillary blood collection tubes
3) Vacuum-assisted blood transfer system
4) Empty storage tube
5) Stabilizing reagents
6) Solid phase absorption/extraction substrate (paper or fabric)

Figure 7:
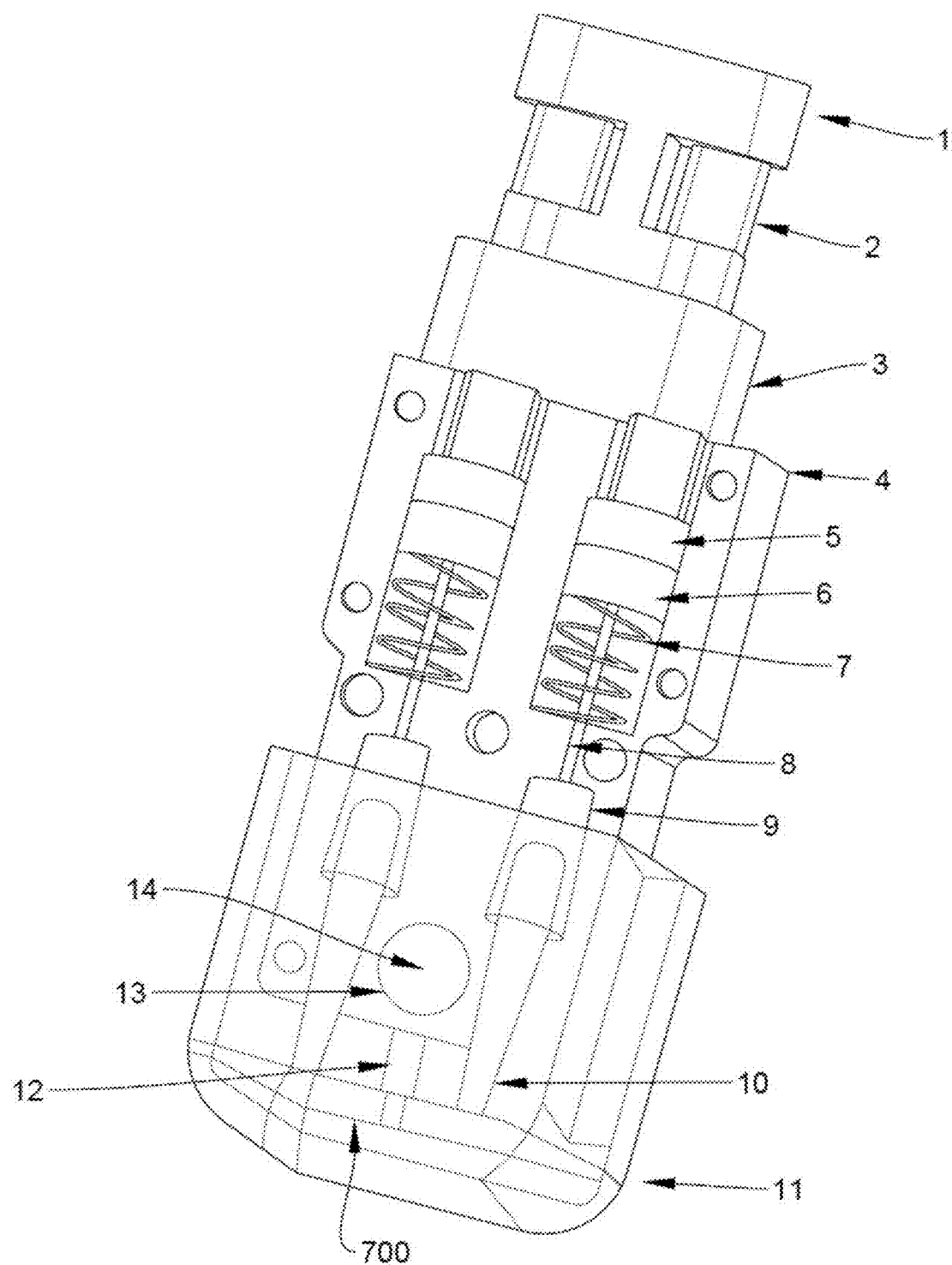
FIG. 7. NUCLEAIR integrated device design with assembled components.
Figure 8:
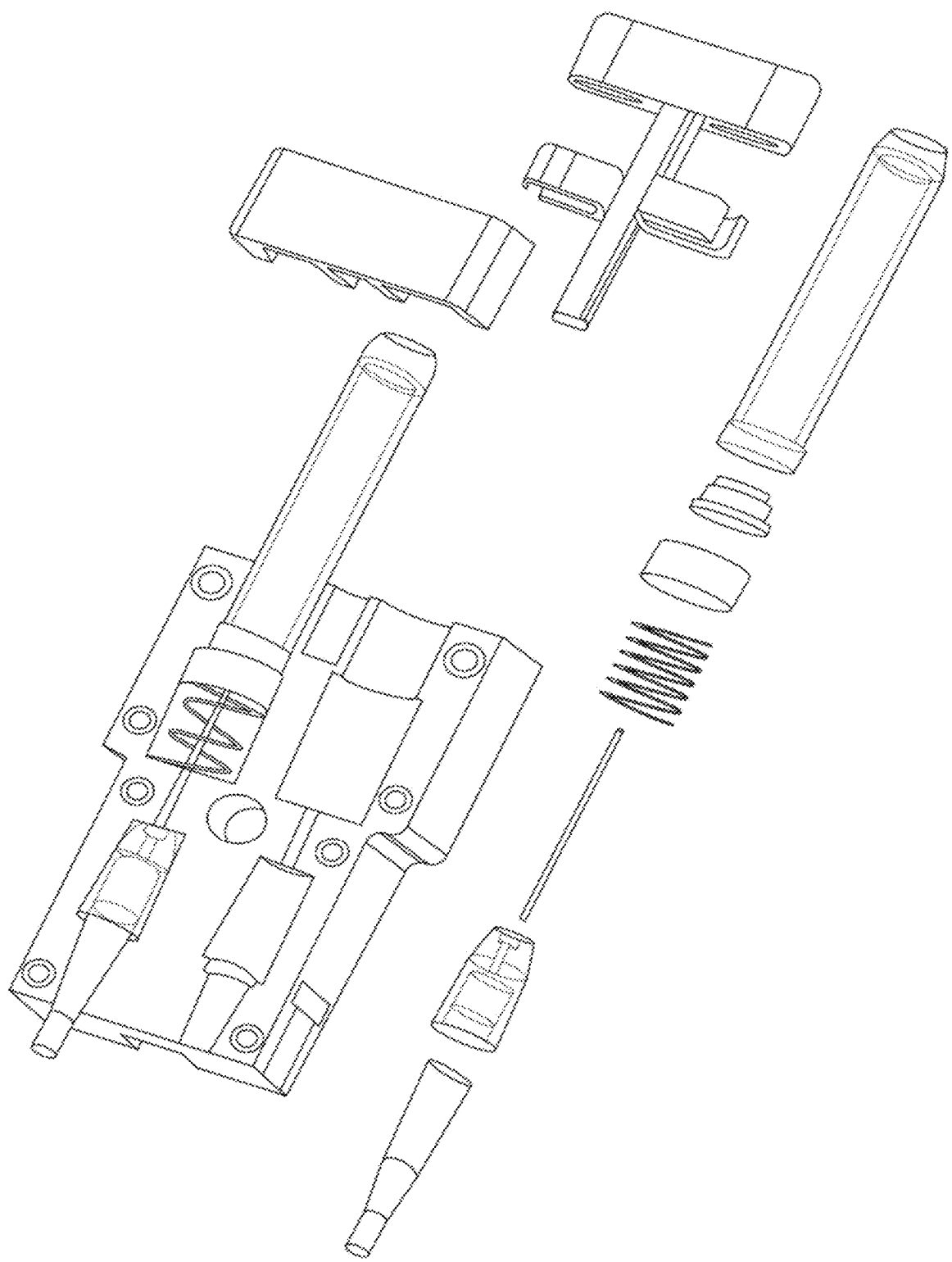
FIG. 8. NUCLEAIR integrated device showing container within the housing and a second collection assemble in a removed from the housing exploded view.

NUCLEAIR integrated device design is shown in FIGS. 6-8 (Exploded View), including with the following element numbers: (1) tube holder; (2) VacuStore tube; (3) Tube Safety; (4) Middle Housing; (5) SepraSeal; (6) Spring Retainer; (7) Compression Spring; (8) 27 G Needle Cannula; (9) Capillary Needle Adapter; (10) Capillary tube (100 µL); (11) Safety cover; (12) Lancet Actuation Nose; (13) Solid Phase Absorption Retainer; (14) Solid Phase Substrate.

The following describes various components of the integrated device:
Manual Surgical Instrument for General Use (e.g. Lancet)
  a. Multiple needle (3-5) plastic lancet (contact-activated)
Capillary Blood Collection Tubes
  a. 100 µl capillary tube coated with EDTA (final assay processing dependent, Gene Expression).
    i. Plastic capillary needle adapter
    ii. ~25 mm long 27 G needle cannula
  b. 100 µl capillary tube coated with Lithium Heparin (final assay processing dependent, cell culture testing).
    i. Plastic capillary needle adapter
    ii. ~25 mm long 27 G needle cannula Vacuum-Assisted Blood Transfer System (Includes 2 Evacuated Glass Storage Tubes).
  a. 1.0 ml 2D Matrix Barcoded Glass tubes (Item #3850, Thermo Scientific)
    i. SepraSeal, Purple Cap (from 96 cap mat Item #4463PUR, Thermo Scientific)
    ii. Plastic spring retainer
    iii. Compression Spring #B4-69 Century Spring
  b. 1.0 ml 2D Matrix Barcode Glass tube (Item #3850, Thermo Scientific)
    i. SepraSeal, Green Cap (from 96 cap mat Item #4463GRE, Thermo Scientific)
    ii. Plastic spring retainer
    iii. Compression Spring #B4-69 Century Spring
  c. Plastic Tube Holder
  d. Plastic Tube Safety
Plastic Storage Tube with Cap
  a. Medical grade plastic with cap, similar to other devices with proposed regulatory classification.
Stabilizing and Preparation Reagents
  a. Reagent volume~300 µl PAXgene solution preloaded in glass tube
  b. Reagent volume~400 µl Cell culture medium preloaded in glass tube
Solid Phase Extraction Substrate
  a. Paper or fabric with sol-gel coating VacuStor tube and capillary-needle assembly are important components of the NUCLEAIR blood collector to transfer the metered blood from the capillary into the VacuStor tube that contains the desired additive reagents. To characterize the quality of the blood transfer, experiments have been conducted to compare the performance of both gene expression assay and cytogenetic micronucleus assay for blood samples processed by the VacuStor transfer, as well as by traditional pipetting.

Figure 9:
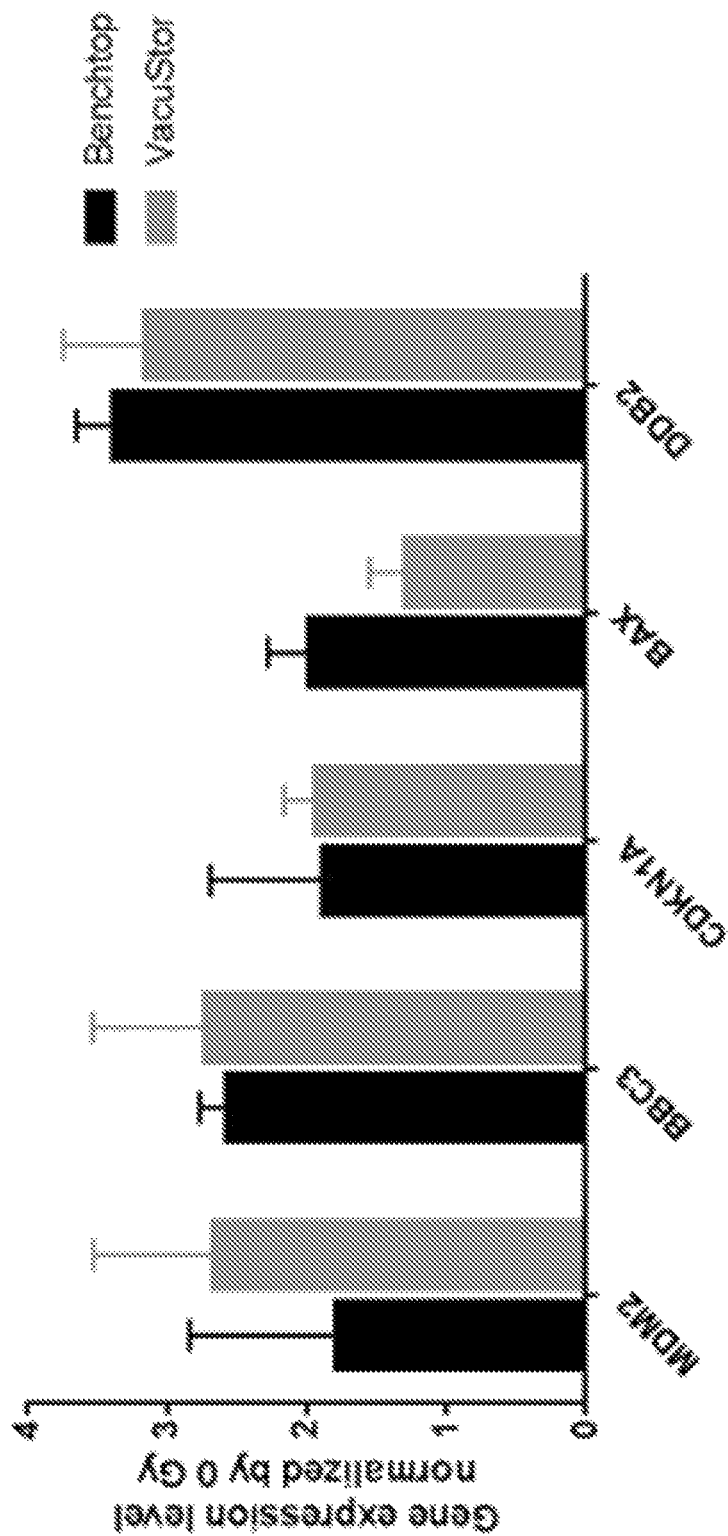
FIG. 9. Gene expression levels at 5 Gy normalized by that at 0 Gy for 5 radiation sensitive genes (MDM2, BBC3, CDKN1A, BAX and DDB2) using blood samples handled by benchtop procedures and VacuStor.

Gene expression assay (FIG. 9): Human blood was purchased and cultured in two 6-well plates in a CO2 incubator at 37° C. for 3-4 hours before irradiation. Irradiation was performed using a cabinet X-ray machine. A total dose of 0 or 5.0 Gy was delivered to the 6-well plates at a dose-rate of 3 Gy/min. The samples were then cultured at 37° C. for another 24 hours. A commercially available gene expression assay chemistry test (DxDirect, DxTerity Diagnostics, CA) was used for multiplex gene expression analysis. 100 µl of sample were collected from the 6-well plates using the capillary-needle assembly and transferred into VacuStor tubes containing 200 µl of DxCollect stabilization buffer. For benchtop controls, 100 µl of diluted blood were directly pipetted into micro-centrifuge tubes containing 200 µl of DxCollect stabilization buffer. Three independent biological replicates were processed for each condition. The final nucleic acid products were analyzed by capillary electrophoresis using an ABI 3130xl genetic analyzer (ThermoFisher Scientific Inc). Gene expression levels were normalized by the nonradiation-responsive genes MRPS5, MRPS18, and CDR2, followed by the normalization of 5 Gy gene expression levels by the 0 Gy levels. FIG. 9 shows the results of 5 Gy gene expression level normalized by 0 Gy for 5 radiation dose-sensitive genes reported in the literature. Gene expression levels were detected for all 5 genes, and showed trends similar to those of measurements by a benchtop pipetting process, indicating that it can be used for gene expression analysis.

Figure 10:
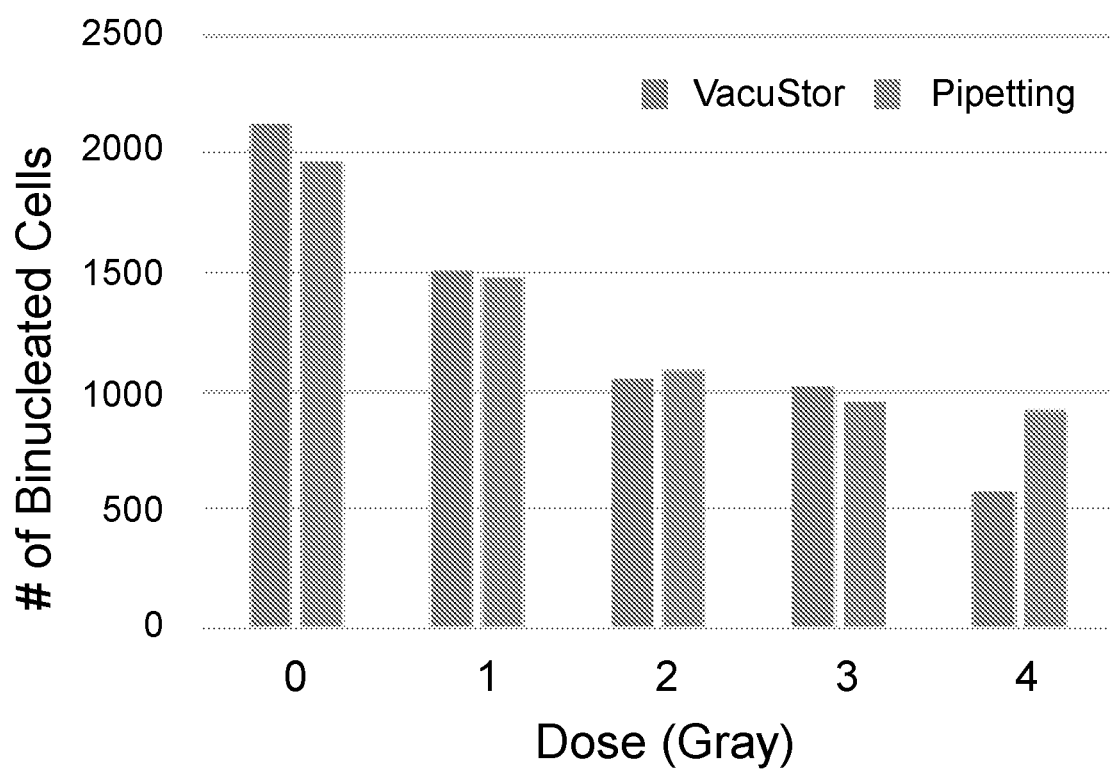
FIG. 10. Number of binucleated cells after culture for blood samples transferred by VacuStore or direct pipetting.
Figure 11:
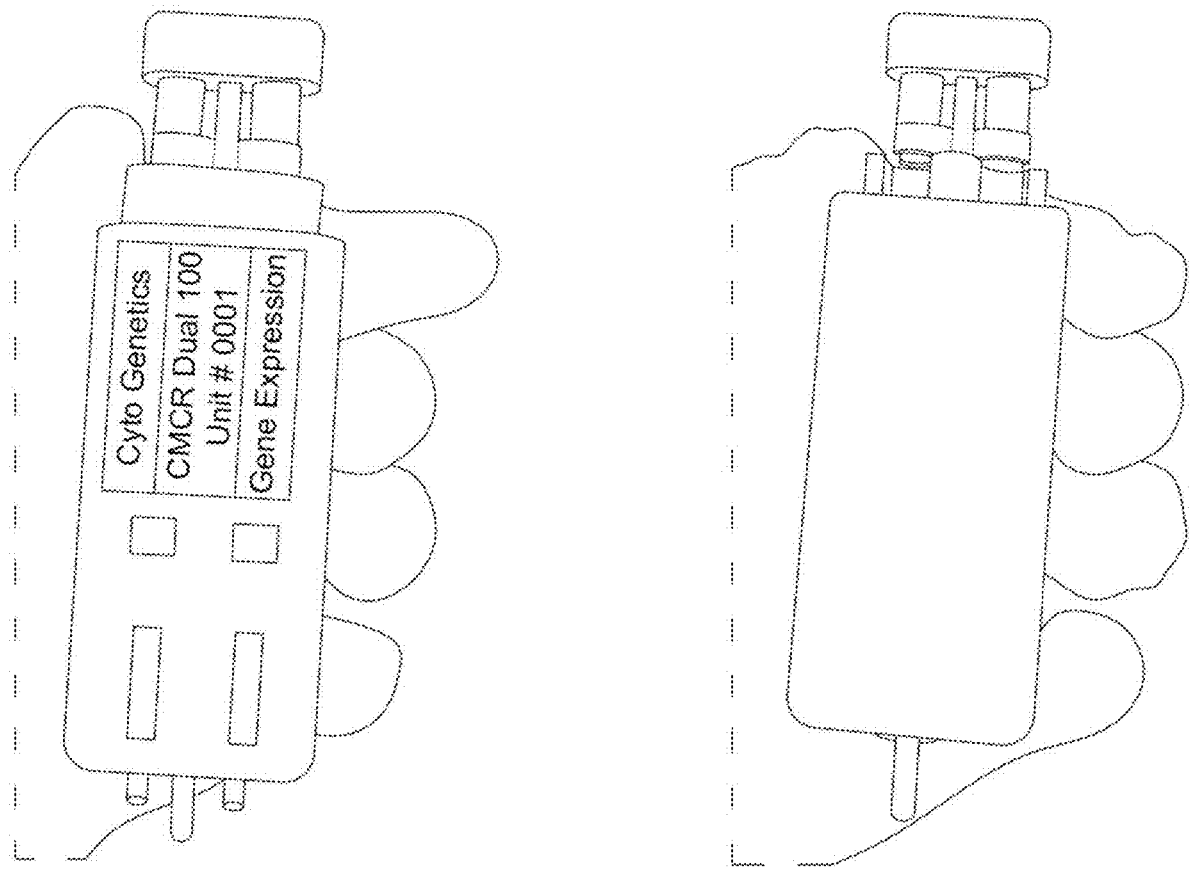
FIG. 11. Photograph of blood collector front (left panel) and rear (right panel).
Figure 12:
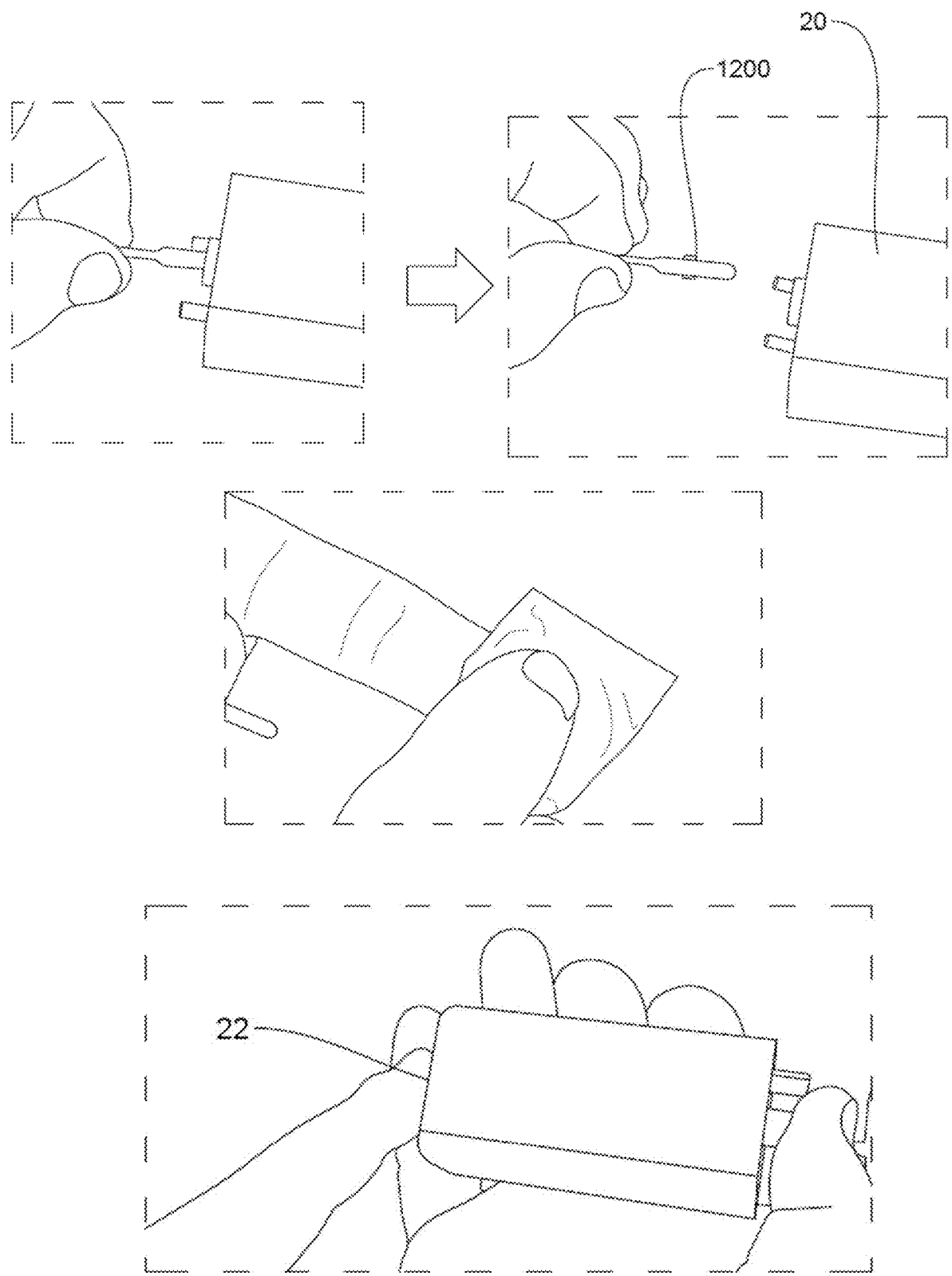
FIG. 12. Remove penetrating member (e.g., lancet) safety, turn 90° and pull away from housing (top panel). Wipe fingertip with alcohol swab (middle panel). Place lancet (end) on fingertip and depress actuator knob (contact activated penetrating member) (lower panel).

Cytogenetic micronucleus assay (FIG. 10): The blood collection components were also tested for cytogenetic micronucleus assay. For blood sample irradiated at 0, 1, 2, 3, and 4 Gy, the blood was either transferred by vacuum into 1.0 ml VacuStor glass tubes containing 0.6 ml of PB-MAX cytogenetic cell culture medium, or by direct pipetting. Then the samples were put inside a shipping box incubator to culture the blood at 37° C. while shipped across country for cytokinesis-blocked micronucleus assay (CBMN) analysis. After received at the recipient address, Cyt-B was added to the sample before 44 hours to block the cytokinesis. At 70 hours, the culture was terminated, and the cells were analyzed for the number of bionucleated cells. FIG. 10 shows the numbers of bionucleated cells at different radiation doses for samples transferred by VacuStor or by direct pipetting. Blood transferred by VacuStor vacuum generated similar bionucleated cells as that by direct pipetting, and the number of bionucleated cells were all much higher than the minimum number of 100 bionucleated cells required by the assay.

Beside the VacuStor and capillary-needle components, we also conducted testing of the integrated blood collector (incl. lancet). The NUCLEAIR device was designed to collect total 200 ul of finger prick blood for both gene expression and CBMN assays (100 ul blood for each assay). Devices have been successfully used to collect, transfer and preprocess the desired amount of blood for downstream assays. For example, the average RNA isolated from the transferred blood for gene expression assay was 557 ng, high enough for the assay.

Example 3: Use of the Device

Figure 13:
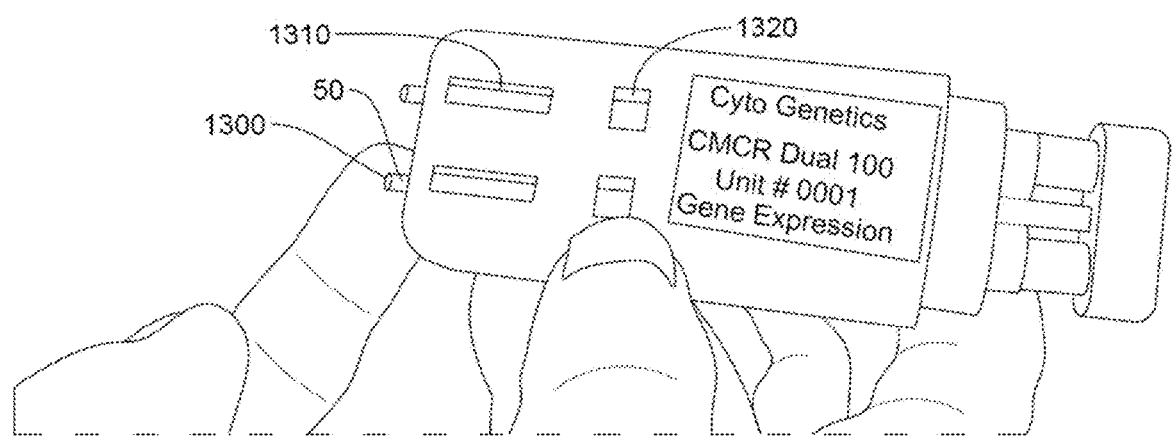
FIG. 13. Gently squeeze fingertip and align first capillary tube with blood droplet. Capillary is horizontal to blood droplet. Observe movement of blood through capillary via observation window. The capillary is full when blood is reaches the final viewing window, move over to second capillary and repeat process. For clarity, the photograph is taken without the blood droplet.
Figure 14:
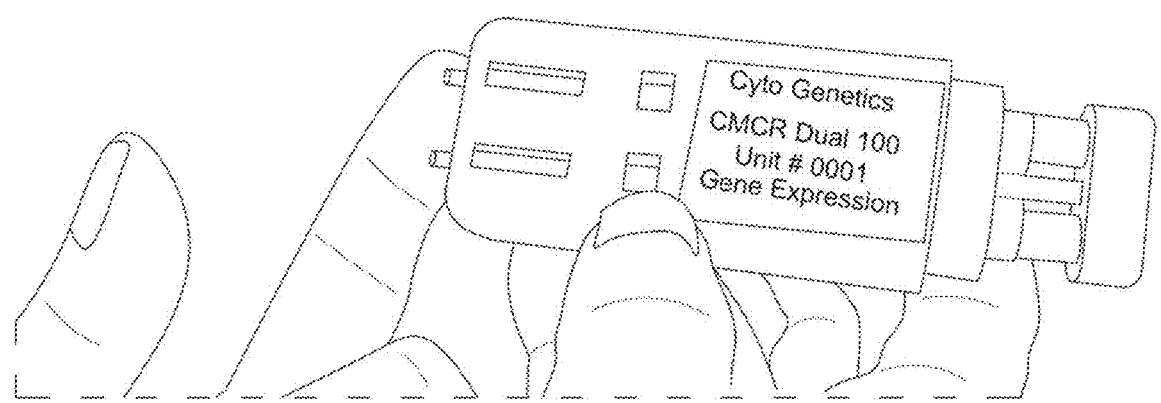
FIG. 14. Same step as FIG. 13, but with a second capillary tube for collection in a second collection tube, including for a different assay.

FIGS. 11-17 illustrate the device and use of the device for collecting multiple blood samples. FIG. 7 illustrates a capillary cover 700 that can cover at least capillary distal ends and, optionally, penetrating member of the blood obtaining assembly. A lancet safety or removable lancet cover 1200 can be removed and pulled away from the housing 20 (FIG. 12 top panels) when the device is ready for use (similarly to capillary cover). The skin surface area is disinfected, such as with an alcohol wipe. The distal end 1210 of the device having the lancet end 1300 is placed against the skin, and a contact-activated member (e.g., 40 of FIG. 1A) engaged to penetrate skin with the lancet. FIG. 13 illustrates the distal end 22 of the capillary tube 50 brought to the blood location and the skin is gently squeezed or milked to facilitate blood movement into the capillary tube. Capillary observation window(s) 1310 allows the user to observe blood movement through the capillary tube. The process is repeated with a second and any number of additional capillary tubes (FIG. 14). Upon sufficient blood fill in the capillary tubes, the tube or container safety 1500 is removed and a blood transfer member engaged, such as a depressible tube holder 1600, to transfer samples into the storage tubes (FIGS. 15-16), such as a vacuum-assisted blood storage container and the container filling may be observed via collection observation windows 1320. The tube holder 1600 may be removed from housing 20, thereby removing the blood storage containers 60 and provided to an appropriate storage container for shipping to a central laboratory analysis. In this manner, provided is a safe, reliable and convenient platform for obtaining multiple separate samples in a one-step fashion that can, as desired, be operated by a user without a need for any other assistance, thereby avoiding a need for another pair of hands. Optionally, the removed containers (FIG. 17A), may be operably connected to blood storage containers 1725, including containers 18 having or corresponding to a solid phase substrate 1730 and/or an extraction substrate 1731 (FIG. 17B).

Example 4: Integrated Finger Prick Blood Self-Collection Device for Radiation Countermeasure We report the development of an integrated finger prick blood collector for self-collecting 100 µl or more blood samples for radiation countermeasure by envelope layer packaging of critical components of the traditional collection kit. A miniaturized vacuum tube system (VacuStor™ system) has been developed to facilitate liquid reagent storage, simple operation and reduced sample contamination. Vacuum shelf life of the VacuStor tube has been analyzed by the ideal gas law and gas permeation theory, and multiple ways to extend vacuum shelf life beyond one year are demonstrated. Self-collection is also demonstrated by healthy donors without any previous finger prick collection experience. The collected blood samples showed similar behavior in terms of gene expression and cytogenetic biodosimetry assays compared to conventionally collected samples. The instant integrated collectors are useful for alleviating sample collection bottleneck after a large scale event, including a biological or radiation event and have other applications where self-collection and liquid reagent sample preprocessing capabilities are beneficial.

In a large scale radioactive event, including a nuclear event in a metropolitan area, it is estimated over a million people would seek information on their exposure levels. Biodosimetry is a critical component in patient triage and management in radiation countermeasure. However, rapid screening of hundreds of thousands of patients in a matter of a few days poses a great challenge to the existing biodosimetry infrastructure. To address this issue, efforts have been made to automate assay protocols for high throughput screening; specific protocols have also been accelerated to reduce the sample-to-answer time (5). But little attention has been paid to the process of sample collection so far.

Blood is a sample type used for many biodosimetry assays (3) due to its rich content and minimal invasiveness for sample collection. However, traditional blood collection using venipuncture, can present a great bottleneck in the collection of hundreds of thousands of samples quickly in radiation response due to its requirement for trained medical personnel that may not be available in the chaotic aftermath of a nuclear event. To meet the required surge in capacity, a self-collection device is highly desired.

Finger prick blood collection requires less training and may be self-administered, but there are still multiple challenges to use existing finger prick protocols for self-collection in a radiation emergency. In this example, we show the rationale, design and prototyping of an integrated blood collector, the development of a critical subsystem of the collector, i.e. a miniature vacuum tube system, to be referred as the "VacuStor™" system, as well as testing of the blood collector for self-collection and performance in biodosimetry assays.

Provided herein is a device for simultaneous blood self-collection for multiple biodosimetry assays, including two complementary assays, i.e. gene expression assay and cytokinesis-block micronucleus assay (CBMN). The gene expression assay has a much shorter sample-to-answer time (several hours), but is only valid for the first 1-7 days after the nuclear incident. The cytogenetic CBMN assay can be valid up to 3-6 months after the nuclear event, but it takes over 3 days for the first results to be available. To collect blood samples for the two assays, a predetermined volume of blood (~50-100 µl) needs to be collected for each assay. In addition, the collected blood samples need to be pre-processed after collection for each assay: a RNA stabilization solution is used to lyse the blood and stabilize RNA right after collection for the gene expression assay, and a cell culture medium is used to start blood cell culture immediately after collection and during transportation for the CBMN assay (a novel approach to dramatically reduce the time required for CBMN assay to generate the first dose result).

Components required for a traditional finger-prick collection kit for the two assays include: 1) a lancet to prick finger; 2) two capillaries with desired anticoagulants to collect, measure minute volume of blood, and transfer blood to designated sample tubes; 3) two sample tubes compatible with high throughput liquid handling with desired reagents in each tube; 4) an optional hand warmer to reach large blood volume if needed; 5) an alcohol wipe for finger disinfection; 6) another alcohol wipe (or a sterile gauze pad) to clean the finger after collection; 7) an adhesive bandage to help wound healing and prevent infection. The need for all of these separate components, and associated separate handling and tracking, is avoided in the instant integrated device, including as illustrated in FIG. 1A and in an exploded view of FIG. 18 (illustrating a one lancet, two capillary-needle assembly with two corresponding vacuum collection tubes.

Three main challenges that can hamper successful self-collection of blood for the biodosimetry assays including: First, there are multiple small items in the kit (e.g. the capillaries and tube caps) that can be easily scattered, contaminated and lost during the collection process in the chaotic situation after a nuclear event. Second, the total collected blood volume of 100 to 200 µl will require a finger milking action by the non-pricked hand of the patient that can present challenges for handling/positioning the capillaries simultaneously for blood self-collection. Finally, during the collection process, the sample tube caps need to be removed for blood transfer, which increases the chance of liquid reagent spill and sample contamination.

Figure 18:
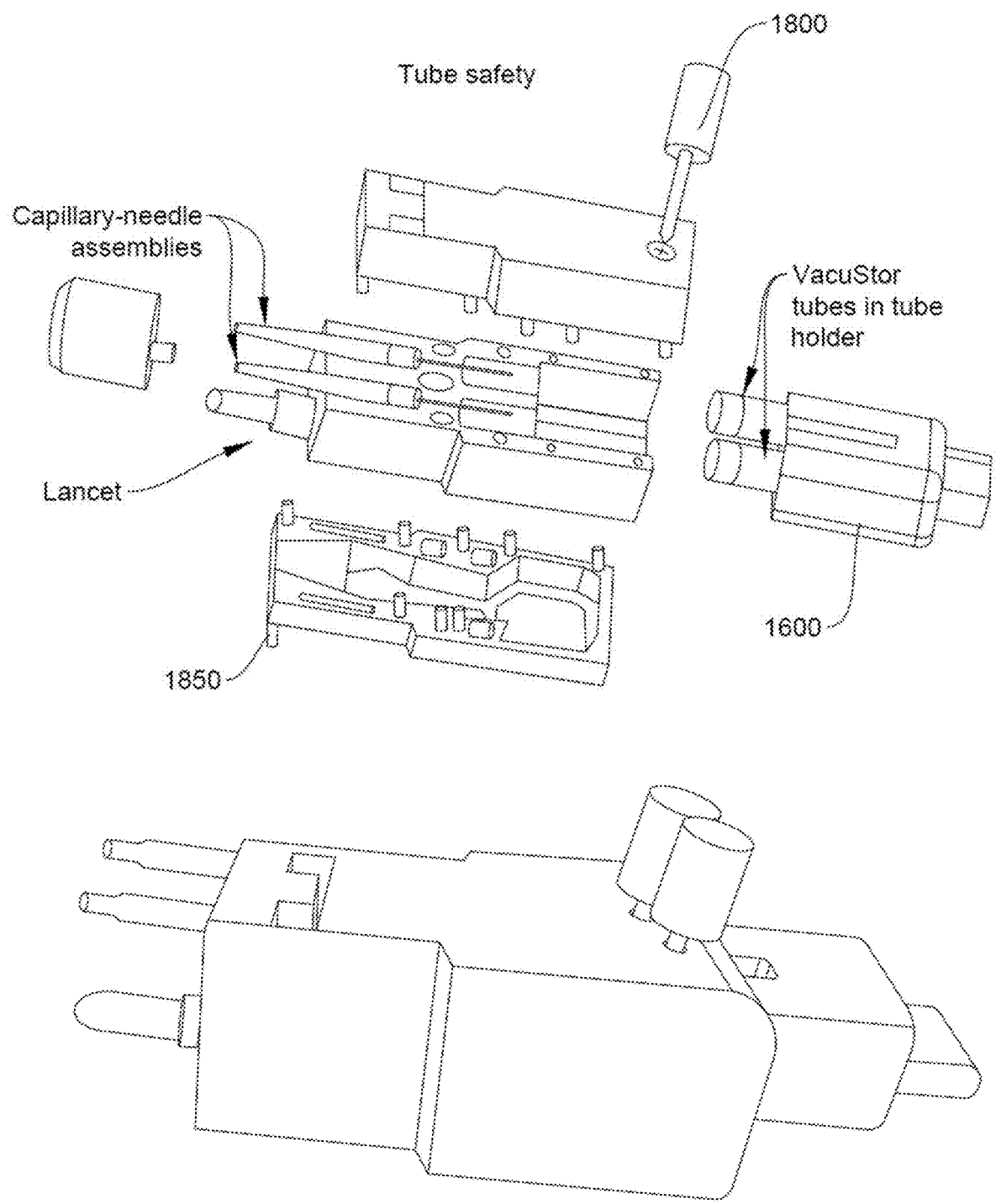
FIG. 18. Exploded view of the integrated blood collector, where one lancet, two capillary-needle assemblies and two VacuStor tubes are integrated by 3D printed parts. A tilting foot facilitates placement of the integrated sample collection device on a flat surface so that the collection capillary tubes are readily accessible to contact blood on skin surface for one-handed handling. Bottom panel is a photograph of an assembled device.

The aforementioned challenges are addressed in an integrated blood collector, including, as shown in FIG. 18, for example. The integrated blood collector uses three envelope layers to hold key components of the kit together to prevent loss/scattering of various components. Furthermore, a single foot 1850 at the bottom of the device can tilt the tips of the capillaries up when the device sits on a flat table surface to aid the blood flowing into the capillaries without the need to handle the device. Finally, a VacuStor system is developed to reduce the handling steps and enable sealed liquid reagent during collection to minimize possibilities for spill and contamination. The VacuStor system comprises a capillary-needle-assembly and a VacuStor tube. The VacuStor tube is a pre-vacuumed storage tube containing the required liquid reagent tailored to the biological fluid sample and/or subsequent assay. After a blood sample is collected into the capillary, the VacuStor tube cap is pierced by the needle, and the vacuum will draw the blood into the tube. The reason for the vacuum tube design for the integrated blood collector is because vacuum tubes have long been used for blood collection and have demonstrated significant improvements in collection safety, speed and sample integrity. They also have liquid storage capability that is convenient and compatible with high throughput systems compared to other integrated microfluidic reagent storage approaches reported before, such as glass ampoules and pouches/blisters.

Geometries of a finger prick lancet (BD Microtainer® Contact-Activated Lancet, blue), two capillary-needle assemblies and two glass VacuStor tubes are measured for the fabrication of the collector parts. The envelope layers, tube holder with safety, and capillary cap are printed by an uPrint SE Plus 3D printer (Stratasys, MN). Press fitting is done by a Carver Press (Wabash, IN) at room temperature. The capillary tilting angle is tested by taping the capillary on a stand under different tilting angle and testing the fluid intake speed and air gap formation using dyed phosphate buffered saline (PBS).

The blood collecting capillaries were either 50 µl or 100 µl, purchased and used as is (Microvette 100 collection capillary, Sarstedt Inc) or cut from existing commercial products (Minivette 50 µl or 100 µl capillary, Sarstedt Inc). Anticoagulant coating of the capillary complies with the target assay protocol, i.e. potassium-EDTA for gene expression assay, and Lithium Heparin for CBMN assay. 27 G 1.5" long hypodermic needles are purchased from EXEUNT International Medical Products. The cannula of the needle is removed from the hub and ground to the appropriate length. Both the capillary and needle cannula were UV glued to an adaptor to complete the capillary-needle assembly. The adaptor was 3D-printed using a Form2 SLA printer from Formlabs. After final assembly the needle cannula was cleaned with a sterile cotton swab and isopropyl alcohol.

Matrix 2D barcoded 1 ml open top glass storage tubes from ThermoFisher Scientific Inc. (Item #3850) that are in 96-rack format and compatible with high throughput liquid handling were used for making VacuStor tubes. The caps were the SepraSeal caps from the same company (Item #4464). For individual VacuStor tube fabrication, a vacuum fixture with a gauge (SMC GZ43-K-01, which measures vacuum relative the environmental pressure) and a feed-through was built to seal the VacuStor tubes with the desired vacuum. For high throughput sealing of 96 VacuStor tubes simultaneously, a custom fixture and a chamber vacuum sealer (ARY VacMaster VP210) are used.

To experimentally test the threshold vacuum for the case of 300 µl of liquid reagent and 100 µl of sample, VacuStor tubes containing 300 µl of PBS at different levels of vacuum were produced. The environmental pressure Penv was measured by a digital barometer (VWR, Cat #10510-922). During VacuStor tube sealing, the sealed volume reduction Vc between initial sealing and fully seated cap was measured by the geometries of the cap. The final VacuStor tube volume Vt was measured by pipetting 1 ml of PBS and measuring the remaining space dimensions of the tube.

With the VacuStor tubes ready, capillary-needle-assembles with cylindrical 100 µl capillaries (Microvette 100, Sarstedt Inc) are used to collect 100 µl of dyed PBS, then pierce the rubber cap of the VacuStor tubes at a horizontal position to transfer the samples to the tubes. The percentage of the sample transfer is measured by the ratio of emptied capillary length to the total capillary length (measured as 35 mm). Three experiments are conducted for each vacuum point.

To characterize the vacuum shelf life of the VacuStor tubes, a hole was drilled in the bottom of the glass tube by sand blasting, then the tube bottom was glued to the SMC vacuum gauge using a low outgassing epoxy glue (Torr Seal from Variant Inc). A similar fixture for sealing individual VacuStor tubes was used to cap the tube under vacuum. Then the vacuum of the VacuStor-gauge assembly was read out over time from the gauge. For low temperature experiments, once the VacuStor-gauge assembly was formed and put into the desired environment, the assembly was allowed to stabilize first before data collection. For Parylene coated caps, 5, 9 or 15.2 µm of Parylene-C coating was coated on the SepraSeal caps by a SCS Labcoater® 2 machine (Specialty Coating Systems, Indianapolis, IN) to form the VacuStor-gauge assembly and monitored at room temperature. The leaking time constants of the VacuStor-gauge assembly ($t_n'$ and $t_o'$) were fitted by the least squares method using GRG Nonlinear Solver from Excel. Because the vacuum gauge has an internal volume Vgauge that is connected with the tube, the real tube time constants $t_n$ and $t_o$ were converted from $t_n'$ and $t_o'$ using equation $t_i = t_i' * V_t/(V_t + V_{gauge})$ where i=n, o. $V_{gauge}$ was measured to be 1450 µl by gluing a syringe to a gauge, then pulling the syringe to a certain volume and calculating $V_{gauge}$ using the ideal gas law from the syringe volume and the vacuum readings from the gauge. After getting $t_n$ and $t_o$, shelf life can be found numerically using Eq. (4) and the initial and threshold vacuums.

To test self-collection of the blood collector, ten devices are fabricated as described before. The capillaries used for the capillary-needle-assemblies were cut from the 50 µl Minivette capillaries (Sarstedt Inc). The VacuStor tubes contained 300 µl PBS in place of required assay liquid reagents. The whole collection-kit included 1) an integrated blood collector, 2) a hand warmer (McKesson Instant Hot Compress, cat #16-9706), 3) an alcohol wipe (First Aid Only H305-200), 4) a Curad Small gauze pad, and 5) a BAND-AID® (Johnson&Johnson). An educational video about conducting self-collection using the collector was made to illustrate the self-collection procedure.

300 µl of PAXgene Blood RNA solution (Qiagen) was used in both microcentrifuge tubes and VacuStor tubes for RNA stabilization. Total RNA was isolated from the collected blood using the PAXgene Blood RNA Kit (Qiagen) following manufacturer's instruction. RNA was quantified using a Nanodrop ND1000 spectrophotometer (ThermoFisher Scientific) and RNA quality was checked by the 2100 Bioanalyzer (Agilent). Sodium-citrate tubes [Becton Dickinson (BD) Catalog-363083] were used for venous blood collection. A gamma source [Gammacell 40 137Cesium irradiator (Atomic Energy of Canada, Ltd., Canada)] at a dose rate of 0.7 Gy/min was used for irradiation. The irradiated samples and the control were incubated at room temperature for 2 h after irradiation before downstream processes. For gene expression comparison, RNA (200 ng) was used for cDNA synthesis using the High-Capacity cDNA Archive Kit (Life Technologies). The cDNA was used for real-time quantitative reverse transcript polymerase chain reaction (qRT-PCR) based gene expression analysis using the Taqman chemistry. Gene expression analysis was carried out for 5 known radiation responsive genes. The gene expression assays (primer/probe sets) were purchased from ThermoFisher Scientific for the following genes: CDKN1A (Hs99999142_m1); BAX (Hs00180269_m1); DDB2 (Hs03044953_m1); FDXR (Hs00244586_m1); MDM2 (Hs01066938_m1), ACTB (Hs99999903_m1). The ΔΔCT method was used to calculate expression relative to controls, normalized against ACTB gene expression.

PB-MAX karyotyping medium (ThermoFisher Scientific Inc.) was used for the CBMN assay. The same Gammacell 40 source used for the gene expression assay was used for irradiation. The dose rate was 0.70 Gy/min. All VacuStor and aliquoted samples were placed in the incubator at 37° C. with 5% $CO_2$. After 24 h of incubation, 250 µl of cell suspension from all samples were transferred into wells of a 96-well plate. Cytochalasin-B was added to the final concentration of 6 µg/ml and samples were cultured for another 30 h. After completion of culturing, cells were processed and analyzed as described before.

Results and discussions: Integrated blood collector prototyping. The concept of packaging small individual parts using 3D printed envelope layers and adaptors is straightforward. But several parts and mechanisms need to be fabricated and implemented in order to realize the functionality of the collector. To prototype the device, three enveloped layers were used to enclose the lancet and two capillary-needle-assemblies into one device housing, as shown in FIG. 18 (top panel). Press fitting is used to assemble the layers due to its simplicity, high strength and low cost, i.e. the peripheral pillar/hole structures on the envelope layers were pressed against each other and the friction force held the layers together. The two VacuStor tubes were housed inside a tube holder and the tube holder could be inserted into the device and slide along two guides printed on the middle envelope layer for tube cap piercing with the needles fluidically connected to the capillary tubes. A holder safety was used to connect the tube holder with the device during storage and prevent accidental cap piercing when in the LOCK position. The sliding action of the tube holder could be enabled by rotating the holder safety 90 degrees to the UNLOCK position. A capillary cap was used to prevent damage and contamination of the capillary tips during storage. All the parts can be printed by 3D printing due to the iterative nature of the design and rapid prototyping capability of 3D printing. FIG. 18 (bottom panel) illustrates a finished integrated blood collector prototype.

To self-collect large volumes of finger prick blood (100 to 200 μl) for the biodosimetry application, we designed the device to sit on a table during collection so that the non-pricked hand of the subject can be used to conduct the milking action as needed. As shown in FIG. 18, the tips of the capillaries are tilted upwards to aid the blood flow into the capillary. Different tilting angles up to 60 degrees are tested. A tilting angle as small as 3 degrees can facilitate sample to flow into the capillary quickly. For tilting angles larger than 30 degrees, the capillary force at the tip was not able to hold the sample against gravitational force and an air gap formed inside the capillary. In this example, a 5-degree tilting angle is used. Currently, the key components of the traditional collection kit (lancet, capillary, high throughput storage tubes with liquid reagents) have been integrated into the collector. Additional items, such as alcohol wipes, gauze pad and adhesive bandage, can also be integrated to the collector to prevent scattering during collection, e.g. attached to the sides of the collector. A hand warmer is expected to be used separately due to its current large size.

The vacuum tube design for the integrated blood collector is not without challenges. Current vacuum tube systems are mainly designed for venipuncture with large tube size, and are not suitable for high throughput bioassays where the storage tube volume is only ~1 ml or less. The shelf life of the small storage tube can be a concern due to vacuum loss from its high surface-to-volume ratio, such as in the recently reported microneedle blood extraction system. Even though vacuum tubes have been used in clinical practice for a long time, no theoretical model has been published regarding the design of air evacuation for blood collection except some empirical observations, such as how blood draw volume varies with altitude. In this example, we use the ideal gas law and gas permeation theory to characterize two parameters that are important to the functionality and practical use of the VacuStor system, i.e. threshold vacuum pressure ($P_{th}$) below which all the blood can be transferred from the capillary into the tube, and vacuum shelf life ($T_{sh}$) of the tube due to vacuum loss.

FIG. 2A shows a picture of a nominal 1.0 ml glass VacuStor tube and a 100 μl capillary-needle-assembly used in this example. FIG. 2B shows the schematics of a VacuStor tube before and immediately after transfer of blood from the capillary into the tube with $P_{in}$ and $P_{in}'$ as the respective tube pressures and $P_{env}$ as the environmental pressure. To have a proper sample transfer:

$$P_{in}' \leq P_{env}$$

Use of the ideal gas law illustrates that $P_{th}$ depends on $V_t$, $V_1$, $V_b$ and $P_{env}$. To test if the ideal gas law can be used to design VacuStor Pth for small tube volume (1 ml or less), imaginary $V_1$ and $V_b$ volumes of 300 μl and 100 μl were used. VacuStor tubes were sealed with different vacuum gauge readings (i.e. $P_{fix}-P_{env}$) of -49, -39, -29, -24, -21, -19 and -14 kPa, where $P_{env}$ was measured as 96.8 kPa and $P_{fix}$ was the vacuum pressure of the fixture during tube sealing. Because there was a tube volume reduction of 77 μl ($V_c$) during VacuStor tube fabrication between initial tube sealing and fully seated cap, the relative tube vacuums ($P_{in}-P_{env}$) were corrected to be -44, -33, -22, -16.4, -13.1, -10.9 and -5.4 kPa using the ideal gas law. FIG. 3 shows the experimental results of how the sample transfer percentage changed with the VacuStor tube vacuum (dots). The threshold vacuum was measured to be -13.1 kPa relative to $P_{env}$. The calculated $P_{th}$ by Eq. (3) was 13.0 kPa (dashed line), indicating a good model of the ideal gas approximation in sub-milliliter regime after considering and accurately measuring all the small volumes involved in the process.

Vacuum shelf life ($T_{sh}$) of the VacuStor tube is related to the pressure increase from gas permeation of the rubber cap (the glass tube used in this study is considered non-gas-permeable). Using gas permeation theory (13) and considering gas composition of air, the normalized relative vacuum $\Delta P'(t)$ can be deduced.

By drilling a hole at the bottom of the VacuStor tube, and gluing it to a vacuum gauge, the normalized relative vacuum pressures over time under multiple conditions were measured experimentally, as shown in FIG. 4. Because the vacuum gauge has an internal volume $V_{gauge}$ of 1.45 ml that will increase the time constants, we denote the measured time constants as $t_n'$ and $t_o'$. It can be seen in FIG. 4 that for a VacuStor tube at room temperature without any cap coating, the vacuum dropped to 47% in 77 days. By fitting the result using determined equations, $t_n'$ and $t_o'$ were found to be 134.4 and 40.3 days respectively. The real $t_n$ and $t_o$ of the tube were calculated as 56.2 and 16.8 days. Assuming an initial vacuum $\Delta P(0)$ of -85 kPa and a threshold vacuum of -20 kPa, the shelf life of the VacuStor tube due to gas leakage was calculated by Eq. (4) to be 67 days, too short to make the device commercially feasible.

For a practical shelf life of VacuStor tubes (e.g. 365 days), we consider the scaling law of the gas leaking time constant, which is on the same order of the shelf life. Determined equations shows that $t_i$ is proportional to V and δ, and inversely proportional to $P_{e,i}$, A and T. Because the miniaturization of the tube usually leads to increased surface to volume ratio (A/V) and smaller cap thickness δ, the shelf life of VacuStor tube can be much shorter than that of larger evacuated tubes. To increase $t_i$, $P_{e,i}$ and T need to be reduced. Reduction of T is usually limited to only ~20%, but lower T can dramatically reduce the permeability of the thermoplastic elastomer cap of the VacuStor tube due to the exponential Arrhenius rule (14). If T cannot be lowered, another common way to reduce gas leakage is by adding low permeable barrier coatings, such as Parylene polymer conformal coating (15). With a two-layered cap, improvement of the gas leaking time is achieved.

FIG. 4 also shows how the normalized relative vacuum changed for VacuStor tubes stored at 5° C. and −10° C., as well as stored at room temperature with 5, 9, 15.2 μm Parylene coating on the cap. It can be seen that, indeed, additional polymer coatings reduce the gas leakage significantly; refrigerator temperature (5° C.) also reduced the gas leakage, similar to a 5 μm Parylene coating; freezer temperature (−20° C.) lowered gas leakage the most, presumably through the much-reduced permeability at low temperature.

FIG. 5 shows the mean values and standard deviations of fitted nitrogen, oxygen leaking time constants for three tubes at each condition for different Parylene polymer thicknesses. The variation is larger for thicker coatings because of the smaller vacuum loss within the experimental time frame due to reduced permeability. The time constants also increase linearly with polymer thickness except for $t_n$ at 15.2 μm. This is consistent with Eq. (5); and the reduction of the $t_n$ at 15.2 μm could come from degraded cap sealing due to stress from the thicker polymer. The $t_n$, $t_o$ for 5° C. without Parylene coating were also plotted in FIG. 4B for comparison. For −20° C., we cannot fit $t_n$ and $t_o$ reliably because the limited vacuum loss due to extremely slow gas leakage and an interruption of the experiment at day 202, but was estimated to be several times longer than that of a 15.2 μm Parylene coating. It should also be noted that because the gases besides Nitrogen occupy only 22% of air, the threshold vacuum may not be reached even if they reached equilibrium with the environment. That means the shelf life of VacuStor will only be determined by the leakage of the nitrogen gas, i.e. $t_n$. In FIG. 4B (gray line), the shelf lives for different conditions were calculated and plotted using mean values of $t_n$, $t_o$ and the previously assumed initial and threshold relative vacuums. The shelf life showed a linear increase with Parylene thickness with a reduction at 15.2 μm, similar to the trend of $t_n$, but not $t_o$ which shows a linear increase for all Parylene thicknesses, consistent with our analysis. It should also be noted that a 9 μm Parylene coating has an expected shelf life of 389 days, long enough for practical applications.

Due to the difference of storage conditions between gene expression and CBMN reagents (RNA stabilization solution stored at room temperature, and cell culture medium stored at −20° C.), it may be necessary that the VacuStor tubes be stored separately from the collector and pre-installed into the collector just before use. For this scenario, a process to extend vacuum shelf life by sealing VacuStor tubes inside a container was tested, where the additional space of the container can extend the vacuum shelf life dramatically, and vacuum bag sealing can also be used which is a much lower cost process than Parylene coating.\

Finger prick blood self-collection has been used at home for diabetes management and research. But the collection volume was low (1 to 15 μl) so that finger milking action was not necessary (16). Our literature search has not revealed any study of self-collection of >100 μl blood from finger prick, although such practice may exist with less demands than the biodosimetry assays (e.g. liquid reagent storage, blood metering etc.). To test the self-collection of our integrated blood collector, first we want to make sure that the desired volume of blood can be generated from a single prick from the collector. We conducted preliminary testing of the blood volume that could be generated by the lancet we used (BD Blue Microtainer contact-activated lancet) using a traditional collection process. 4 out 7 collections did not reach 200 μl without a hand warmer vs. 6 out of 7 collections reached 200 μl using a hand warmer. To minimize the chance that a single prick may not generate enough blood for the collector, we tested the integrated blood collector with a collection volume of total 100 μl (two 50 μl capillaries) with a hand warmer.

Ten healthy donors between ages of 20 to 51 without any finger prick blood collection experience were recruited. They were asked to self-collect the blood samples into VacuStor tubes after watching an instructional video. The instructional video was made because the collection process still involves multiple steps and we considered that video education would be more effective than written instructions, as reported previously (17). Table 1 shows the results of the test, including donor number, gender, pricked hand/finger, capillary size and collected blood volume. The collected blood volume into the VacucStor tubes was measured by weighing the tubes before and after collection and converting the weight to volume using a blood density of 1.060 g/ml. All 10 donors were able to successfully collect blood themselves using the collector. Among the 20 capillary-needle-assemblies from the 10 devices, 18 were able to collect blood and transfer the blood into the VacuStor tubes by vacuum. The blood volume collected ranged from 43.1 to 50.9 μl, with mean±SD of 47.1±2.1 μl. No significant blood was left in the capillaries after transfer. We attribute the blood volume variation to our fabrication process where the capillary was manually cut out from a commercial product. For two capillary-needle-assembles, the capillaries were not able to collect the blood, possibly due to clogging of the assembly during the fabrication process.

Even though all donors successfully collected blood themselves, it was not without issues. Two out of ten donors forgot to disinfect their fingers before prick. Two donors also had blood dripped to the back of their hands due to upward finger positions. These will be further improved through instruction improvement and possible device design. Even with these issues, however, no infection is reported from the donors.

In order to further validate the integrated blood collector for biodosimetry applications, we compared samples collected by the device to those by traditional method using both gene expression and CBMN assays.

Figure 19:
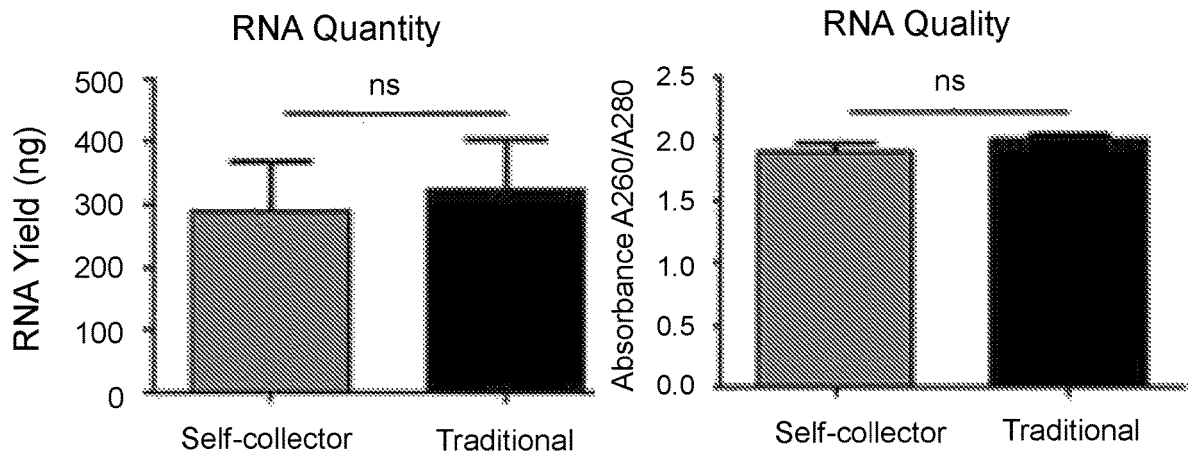
FIG. 19. Characterization of self-collected samples for gene expression and cytogenetic biodosimetry assays. Comparison of quantity (left—RNA Yield) and quality (right—absorbance) of RNA isolated from blood using traditional method and the self-collector. Electropherograms (not shown) demonstrate integrity of RNA by the self-collectors (RINs=7.0-8.5, comparable to traditional method).

For gene expression assay, quality and quantity of isolated RNA were first compared using non-irradiated blood. 50 μl of blood was collected into microcentrifuge tubes containing RNA stabilization solution by traditional method from three healthy donors. 50 μl of blood was also collected into VacuStor tubes containing the same reagent by the integrated blood collectors from the same donors at the same time. RNA was isolated and the results are shown in FIG. 19. No statistically significant difference (P>0.05) was found between the two methods in terms of the quantity or quality of the isolated RNA. 300-400 ng of total RNA was isolated from 50 μl of blood using the device, which is comparable to that by traditional fingerpick collection method. The quality of RNA was also characterized by absorbance ratio at 260 and 280 nm and was found to be comparable to that by the traditional method. Electropherogram of some of the RNAs isolated from samples collected by the devices; the RINs (RNA integrity number) of the RNAs as determined by an Agilent Bioanalyzer were found to be between 7.0-8.5, which is of acceptable quality for most downstream applications.

Besides the RNA quantity and quality, experiments are conducted to see if sample collection by the integrated blood collector would alter radiation-induced gene expression comparing to traditional method using a real-time qRT-PCR assay. Five radiosensitive genes (CDKN1A, BAX, DDB2, MDM2 and FDXR) reported in the literature (18) are selected for the experiment. Because it is complicated to irradiate blood inside the collector, venous blood is collected from three healthy donors into two sample tubes. One tube is irradiated to a dose of 3 Gy, and the other tube was used as a sham-irradiated control. After allowing time for gene expression changes to occur, the irradiated and control bloods are collected into the VacuStor tubes containing the RNA stabilization solution through the device, or pipetted into microcentrifuge tubes containing the same solution. The gene expression levels of the 3 Gy samples relative to those of unirradiated controls are measured using both the traditional method and through the device. The housekeeping gene ACTB was used as the normalization control. We were able to detect expression of all 5 genes using the collector. The gene expression levels and radiation response trends measured using the device are similar to measurements made by a traditional pipetting process (no significant difference in expression at P>0.05), indicating that blood collection by the collector can be used for gene expression analysis.

Finally, a gene expression comparison between the traditional method and the integrated blood collector using a ligation based assay chemistry (DxDirect®, DxTerity Diagnostics, CA) was also conducted, and the gene expressions were also found to be "not significant" between the two methods, indicating a broader application of the device for different assay chemistries.

Figure 20:
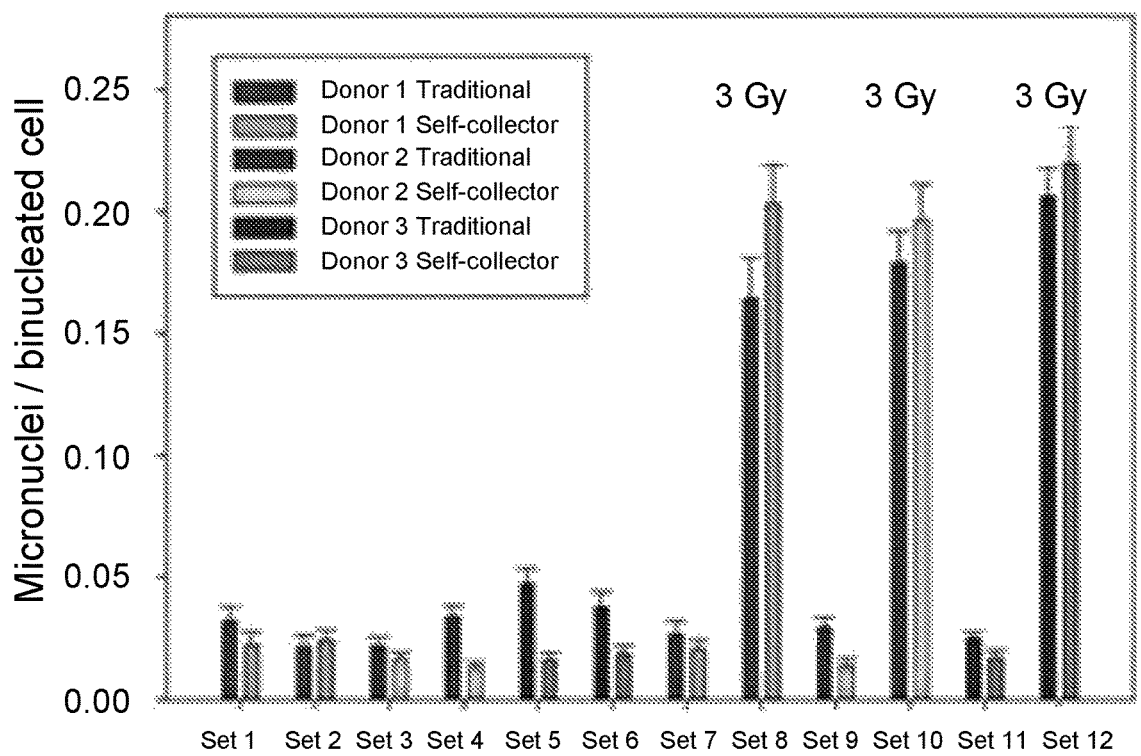
FIG. 20. Micronuclei per binucleated cell for samples collected by traditional method or the integrated self-collector. The numbers are below 0.05 for all non-irradiated samples, with no statistically significant difference between traditional and self-collector obtained samples.
Figure 21:
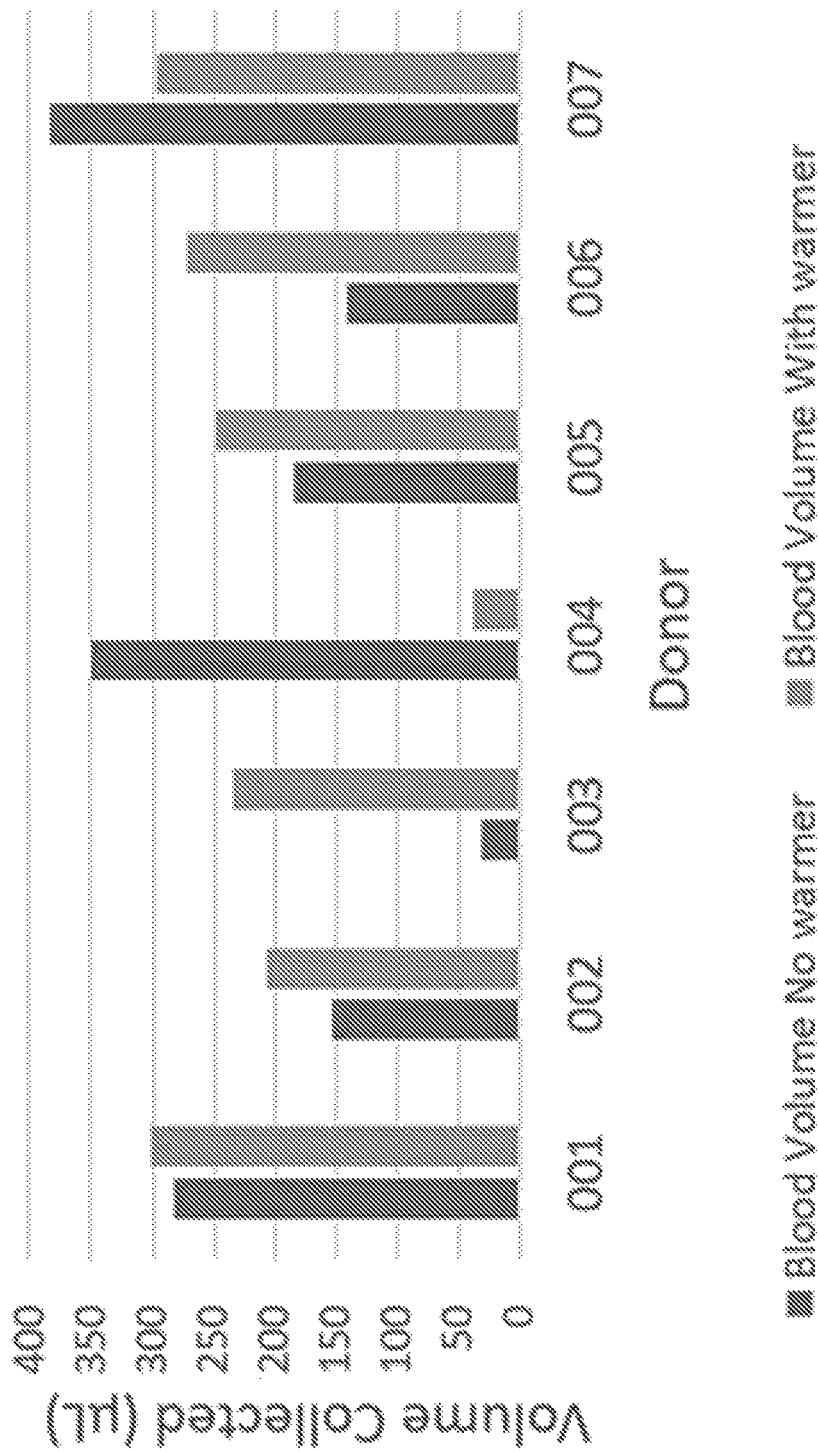
FIG. 21. Lancet blood collection with and without a hand warmer from 7 donors.

Cytogenetic CBMN assay: We first compared micronuclei level for non-irradiated finger prick samples. For traditional finger prick collection, 150-200 µl of blood per donor from three healthy donors were collected into heparinized tubes; then 25 µl was prepared in aliquot into the 1 ml glass Matrix tube containing 225 µl of culture medium for CBMN assay. For the integrated blood collector, six 50 µl blood samples (two samples per donor from the same three donors) were also collected at the same time by the collector into VacuStor tubes containing 550 µl culture medium. The level of micronuclei per binucleated cell was measured for all the non-irradiated samples, as shown in FIG. 20 (sets 1-6). The numbers were all below 0.05, which is an acceptable background.

For irradiated samples, venous blood was collected from the donors for the same reason as mentioned in the gene expression assay. The blood was then split to two, and irradiated at 0 and 3 Gy respectively by gamma-rays. Then irradiated samples and the controls either went through the collector device to be collected into VacuStor tubes, or were in aliquot into the 1 ml matrix tubes as described for the non-irradiated finger prick sample experiment above. The number of micronuclei per binucleated cell was assayed by CBMN, as shown in FIG. 20 (sets 7-12). The 0 Gy samples prepared with or without the collector still showed the micronuclei level to be below 0.05. The 3 Gy samples showed no significant difference in the micronuclei level when they were prepared with or without use of the collector for all 3 donors (p<0.05). These results indicate that the integrated blood collector can be used for blood collection for cytogenetic analysis to estimate radiation doses.

An integrated finger prick blood collector with liquid reagent storage capability for high throughput sample self-collection and pre-processing suitable for use with large-scale radiation biodosimetry is demonstrated. A critical sub-system of the collector, the VacuStor system, has been characterized and a methodology for analyzing evacuated tubes for blood collection has been developed. We have shown that the threshold vacuum of the VacuStor tube can be deduced by the ideal gas approximation. Through gas permeation theory, different ways to extend the shelf life of the VacuStor tube over a year were developed. The device has been successfully tested for self-collection, and the collected blood was also successfully demonstrated for gene expression and cytogenetic biodosimetry assays. Besides radiation countermeasures, the device could be used for other applications where blood may need to be self-collected by individuals (e.g. at home or in a disaster theater) with liquid reagent pre-processing and sent to a central laboratory for analysis. The vacuum tube methodology developed here can be used to guide the development of other miniature vacuum actuated devices.

VacuStor tube formation: A fixture can fabricates VacuStor tubes one at a time. The fixture was made with a plastic tube with two rubber stoppers sealing at each end. To seal a VacuStor tube, the Matrix storage tube with liquid reagent seated on the bottom stopper, the tube cap seated on a plastic rod through the top stopper, and the tube can be sealed by pushing the cap to the opening of the tube. A vacuum port was used to pump vacuum. A vacuum gauge (GZ43-K-01, SMC Corporation) was used to read the vacuum relative to the environmental pressure. 96 VacuStor tubes can be made in a rack at the same time. A fixture was made to have all the caps on a mat to suspend on top of the open tubes. The fixture was put inside a vacuum sealing bag and sealed by the chamber vacuum sealer (VacMaster VP210). After vacuuming and bag sealing, the chamber was opened, and all the tube caps were pressed onto the tube openings by atmosphere pressure to seal all the VacuStor tubes.

VacuStor tube vacuum losses can be calculated or determined for different construction, such as for a two-layered cap, vacuum bag sealing of the VacuStro tubes inside a container, with corresponding numerical calculation that can be compared to experimentally-tested results for model validation.

Any of the devices and systems provided herein may be adapted to collection of large volume (e.g., >100 µL) samples, including be incorporating a plurality of lancets, such as a lancet array 2200 illustrated in FIG. 22. The lancet may be formed of a plastic. FIG. 22 has optical images of a design geometry of the plastic needles, with illustrations of the device testing methods used in production of the devices. Prototype plastic needles can be tested for penetration depth using the silicone membranes (60-70 shore (A) hardness) (see punctuation depth (in mm) at the bottom panel of FIG. 22). The silicone membranes are clear and allow non-contact measurement of the penetration depth.

References for Example 4

1. Coleman C N, Hrdina C, Bader J L, Norwood A, Hayhurst R, Forsha J, et al. Medical Response to a Radiologic/Nuclear Event: Integrated Plan From the Office of the Assistant Secretary for Preparedness and Response, Department of Health and Human Services. Ann Emerg Med. 2009 February; 53(2):213-22.
2. Grace M B, Moyer B R, Prasher J, Cliffer K D, Ramakrishnan N, Kaminski J, et al. Rapid Radiation Dose Assessment for Radiological Public Health Emergencies: Roles of Niaid and Barda. Health Phys. 2010 February; 98(2):172-8.
3. Sullivan J M, Prasanna P G S, Grace M B, Wathen L K, Wallace R L, Koerner J F, et al. Assessment of Biodosimetry Methods for a Mass-Casualty Radiological Incident: Medical Response and Management Considerations. Health Phys. 2013 December; 105(6):540-54.
4. Repin M, Pampou S, Karan C, Brenner D J, Garty G. RABiT-II: Implementation of a High-Throughput Micronucleus Biodosimetry Assay on Commercial Biotech Robotic Systems. Radiat Res. 2017 April; 187(4):492-8.
5. Repin M, Pampou S, Garty G, Brenner D J. RABiT-II: A Fully-Automated Micronucleus Assay System with Shortened Time to Result. Radiat Res. 2019 March; 191(3):232-6.
6. Bush V, Cohen R. The evolution of evacuated blood collection tubes. Lab Med. 2003 April; 34(4):304-10.
7. Hoffmann J, Mark D, Lutz S, Zengerle R, von Steffen F. Pre-storage of liquid reagents in glass ampoules for DNA extraction on a fully integrated lab-on-a-chip cartridge. Lab Chip. 2010; 10(11):1480-4.
8. Chen D, Mauk M, Qiu X, Liu C, Kim J, Ramprasad S, et al. An integrated, self-contained microfluidic cassette for isolation, amplification, and detection of nucleic acids. Biomed Microdevices. 2010 August; 12(4):705-19.
9. Czurratis D, Beyl Y, Grimm A, Brettschneider T, Zinober S, Laermer F, et al. Liquids on-chip: direct storage and release employing micro-perforated vapor barrier films. Lab Chip. 2015; 15(13):2887-95.
10. DuPont. Design Handbook for DuPont Engineering Polymers, Module 1: General Design Principles. 1992.
11. Li C G, Dangol M, Lee C Y, Jang M, Jung H. A self-powered one-touch blood extraction system: a novel polymer-capped hollow microneedle integrated with a pre-vacuum actuator. Lab Chip. 2015; 15(2):382-90.
12. MacNutt M J, Sheel A W. Performance of evacuated blood collection tubes at high altitude. High Alt Med Biol. 2008; 9(3):235-7.
13. VANAMERONGEN G J. The Permeability of Different Rubbers to Gases and its Relation to Diffusivity and Solubility. J Appl Phys. 1946; 17(11):972-85.
14. Komatsuka T, Nagai K. Temperature Dependence on Gas Permeability and Permselectivity of Poly(lactic acid) Blend Membranes. Polym J. 2009; 41(5):455-8.
15. Sawano S, Naka K, Werber A, Zappe H, Konishi S. Sealing method of PDMS as elastic material for MEMS. Mems 2008: 21st Ieee International Conference on Micro Electro Mechanical Systems, Technical Digest. 2008.
16. Hirshfield S, Teran R A, Downing M J, Jr, Chiasson M A, Tieu H V, Dize L, et al. Quantification of HIV-1 RNA Among Men Who Have Sex With Men Using an At-Home Self-Collected Dried Blood Spot Specimen: Feasibility Study. JMIR Public Health Surveill. 2018 Nov. 1; 4(4):e10847.
17. Shah R F, Gupta R M. Video instruction is more effective than written instruction in improving inhaler technique. Pulm Pharmacol Ther. 2017 October; 46:16-9.
18. Paul S, Amundson S A. Development of gene expression signatures for practical radiation biodosimetry. Int J Radiat Oncol Biol Phys. 2008 Jul. 15; 71(4):1236-44.
19. Xu L, Lee H, Jetta D, Oh K W. Vacuum-driven power-free microfluidics utilizing the gas solubility or permeability of polydimethylsiloxane (PDMS). Lab Chip. 2015; 15(20):3962-79.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Whenever a range is given in the specification, for example, a number range, a volume range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLE 1

Results of the integrated blood collector self-collection testing.

| Donor # | Gender | Hand/ Finger | Cap-illaries | Before (g) | After (g) | Blood Volume (µl) |
|---|---|---|---|---|---|---|
| 1 | F | L/3 | 50 µl × 2 | 1.8881 | 1.9348 | 44.1 |
|   |   |     |            | 1.8722 | 1.9190 | 44.2 |
| 2 | M | L/3 | 50 µl × 2 | 1.87213 | 1.92251 | 47.5 |
|   |   |     |            | 1.86793 | 1.92090 | 50.0 |
| 3 | M | L3 | 50 µl × 2 | 1.87618 | 1.92787 | 48.8 |
|   |   |    |            | 1.87569 | 1.92646 | 47.9 |
| 4 | M | L4 | 50 µl × 2 | 1.90384 | 1.95384 | 47.2 |
|   |   |    |            | 1.89575 | 1.94385 | 45.4 |
| 5 | F | L4 | 50 µl × 2 | 1.89249 | 1.94239 | 47.1 |
|   |   |    |            | 1.89922 | 1.9504  | 48.3 |
| 6 | F | R3 | 50 µl × 2 | 1.89658 | 1.94827 | 48.8 |
|   |   |    |            | 1.90226 | 1.95273 | 47.6 |
| 7 | M | L3 | 50 µl × 2 | 1.86968 | 1.91537 | 43.1 |
|   |   |    |            | 1.88129 | 1.93077 | 46.7 |
| 8 | M | L3 | 50 µl × 2 | 1.88586 | failed  | failed |
|   |   |    |            | 1.88879 | 1.9363  | 44.8 |
| 9 | F | L3 | 50 µl × 2 | 1.91799 | failed  | failed |
|   |   |    |            | 1.85468 | 1.90059 | 43.3 |
| 10| F | L3 | 50 µl × 2 | 1.89444 | 1.94838 | 50.9 |
|   |   |    |            | 1.88652 | 1.93616 | 46.8 |

We claim:

1. An integrated sample collection device for self-collection and analytical pre-processing of a biological fluid sample from a user comprising:
    a housing configured to be held by a user;
    a foot at the bottom of the housing configured to tilt the integrated sample collection device while it rests on a flat surface at an upward tilting angle of 3 degrees to 30 degrees;
    a contact-activated penetrating member disposed at least partially in the housing and configured to penetrate skin;
    a capillary tube at least partially disposed in the housing and configured to collect blood released from the penetrating member that penetrates the skin;
    a vacuum-assisted blood collection container fluidically connected to the capillary tube for receiving at least a portion of the collected blood by:
    an adapter connected to a proximal end of the capillary tube;
    a transfer needle connected to the adapter;
    a cap having a low permeable barrier coating and a thickness connected to the vacuum-assisted blood collection container, wherein the transfer needle is configured to controllably pierce the cap of the vacuum-assisted blood collection container to provide blood to the vacuum-assisted blood collection container by a vacuum generated by the vacuum-assisted blood collection container and the low permeable barrier coating is configured to prevent leakage out of the vacuum-assisted blood collection container; wherein:
        the vacuum generated by the vacuum-assisted blood collection container is less than or equal to −13.1 kPa relative to environmental pressure; and
        the transfer needle comprises a bevel and a depth of the bevel is shorter than the thickness of the cap of the vacuum-assisted blood collection container;
    one or more stabilizing and pre-processing agents for initiating an analytical pre-processing of the collected blood in the capillary tube, the vacuum-assisted blood collection container, or both, wherein:
    the stabilizing agent comprises an RNA stabilization solution configured to lyse red blood cells and stabilize RNA immediately after collection; and
    the pre-processing agent is selected from the group consisting of a cell culture media, a PCR reagent, a label, and a binding agent so that at least a portion of the biological fluid sample undergoes one or more pre-processing steps during transport to a laboratory to decrease a sample processing time at a laboratory.

2. The integrated sample collection device of claim 1 that is a multiple sample collection device further comprising:
    two capillary tubes; and
    two vacuum-assisted blood collection containers, with a first capillary tube fluidically connected to a first vacuum-assisted blood collection container and a second capillary tube fluidically connected to a second vacuum-assisted blood collection container;
    the first vacuum-assisted blood collection container contains the RNA stabilization solution configured to lyse red blood cells and stabilize RNA immediately after collection in the first vacuum-assisted blood collection container for pre-processing of a gene expression assay;
    the second vacuum-assisted blood collection container contains the cell culture medium configured to initiate a blood cell culture immediately after collection and during a transport time for pre-processing of a cell culture based assay.

3. The integrated sample collection device of claim 1, further comprising a plurality of contact-activated penetrating members configured to penetrate skin at a plurality of distinct locations, wherein the plurality of contact-activated penetrating members correspond to a lancet array.

4. The integrated sample collection device of claim 3, further comprising a plurality of capillary tubes to collect blood from a plurality of distinct skin locations and/or to store blood in a plurality of distinct vacuum-assisted blood collection containers.

5. The integrated sample collection device of claim 1, wherein the low permeable barrier coating comprises a parylene polymer conformal coating.

6. The integrated sample collection device of claim 2, wherein the first and second vacuum-assisted blood collection containers are configured to provide pre-processing in each of the first and second blood collection containers during shipping to the laboratory to decrease laboratory processing time to determine a base indicator of a radiological exposure in a nuclear or a radiological incident.

7. The integrated device of claim 1, wherein at least one vacuum-assisted blood collection container comprises: a solid phase absorption member; or an extraction substrate.

8. The integrated sample collection device of claim 1, wherein the vacuum-assisted blood collection containers are removably connected to the housing.

9. The integrated sample collection device of claim 8, wherein the first and second vacuum-assisted blood storage containers are positioned in a container holder, and the container holder with the first and second vacuum-assisted blood storage containers are configured for insertion into and removal from the housing.

10. The integrated sample collection device of claim 1, further comprising one or more blood storage containers operably connected to the first and/or second vacuum-assisted blood collection containers, wherein blood from the first and/or second vacuum-assisted blood collection containers is introduced to the one or more blood storage containers, wherein at least one of the blood storage containers comprise a solid-phase substrate such as a membrane.

11. The integrated sample collection device of claim 1, further comprising a capillary observation window to view flow of collected blood along the capillary tube.

12. The integrated sample collection device of claim 1, further comprising a blood collection observation window to view collection of blood in the vacuum-assisted blood collection container.

13. The integrated sample collection device of claim 1, wherein the stabilizing agent further comprises an anticoagulant that coats a lumen wall of the capillary tube.

14. The integrated sample collection device of claim 1, wherein the penetrating member comprises a lancet, wherein the lancet is formed of a metal or a plastic.

15. The integrated sample collection device of claim 1, wherein the biological fluid sample comprises whole blood.

16. The integrated sample collection device of claim 1, further comprising a container safety in operable communication with the vacuum-assisted blood collection container to prevent unwanted actuation movement of the vacuum-assisted blood collection container toward the capillary tube.

17. The integrated sample collection device of claim 1, further comprising a removable capillary cover to cover a distal end of the capillary tube and a removable lancet cover that covers a distal penetrating end of the lancet when the device is not in use.

18. The integrated sample collection device of claim 1, configured to receive a user-force against a distal end of the housing and/or proximal end of the housing to actuate a motion of the penetrating member to pierce a skin surface.

19. The integrated sample collection device of claim 1, further comprising a foot connected to or extending from the housing to provide a device relative to horizontal angle that is greater than or equal to 3 degrees and less than or equal to 30 degrees for a device resting on a horizontal surface with the foot and the housing in physical contact with the horizontal surface.

20. A method of sampling a blood sample, the method comprising the steps of:
 transporting the blood collection container from the device of claim 1 to a laboratory for sample processing, wherein the blood collection container contains a blood sample from a user;
 wherein during the transporting, at least a portion of the sample undergoes one or more pre-processing steps, thereby decreasing sample processing time by the laboratory.

21. The integrated sample collection device of claim 2, wherein the cell-culture based assay comprises a cytokinesis-block micronucleus.

22. The integrated sample collection device of claim 1, wherein the low permeable barrier coating has a thickness greater than or equal to 9 µm and less than 15.2 µm.

23. An integrated sample collection device for self-collection of a blood sample from a user comprising:
 a housing configured to be held by a user;
 a foot at the bottom of the housing configured to tilt the integrated sample collection device while it rests on a flat surface at an upward tilting angle of 3 degrees to 30 degrees;
 a contact-activated penetrating member disposed at least partially in the housing and configured to penetrate skin;
 a first and a second capillary tube disposed in the housing and each having a distal end configured to collect blood released from the penetrating member that penetrates the skin and an actuatable penetrating proximal end;
 a first vacuum-assisted blood collection container at least partially disposed in the housing and configured to temporarily fluidically connect to the first capillary tube to receive at least a portion of the collected blood from the first capillary tube upon an actuation force applied to the first vacuum-assisted blood collection container;
 a second vacuum-assisted blood collection container at least partially disposed in the housing and configured to temporarily fluidically connect to the second capillary tube to receive at least a portion of the collected blood from the second capillary tube upon an actuation force applied to the second vacuum-assisted blood collection container;
 wherein the first and the second vacuum-assisted blood collection container generate a vacuum and the vacuum is less than or equal to −13.1 kPa relative to environmental pressure;
 wherein the first and the second vacuum-assisted blood collection containers are fluidically connected to the first and the second capillary tubes for receiving at least a portion of the collected blood by:
 a first adapter and a second adapter connected to a proximal end of the first and the second capillary tubes;
 a first and a second transfer needle connected to the first and the second adapter;
 a first cap and second cap having a low permeable barrier coating and a thickness connected to the first and the second vacuum-assisted blood collection container; wherein
  the first and the second transfer needles comprise a bevel and a depth of the first and second transfer needle bevel is shorter than the thickness of the first and the second cap;
 a stabilizing agent for stabilizing collected blood in the first and/or second capillary tube, the first and/or second vacuum-assisted blood collection container, or both;

wherein the first vacuum-assisted blood collection container contains the stabilizing agent that is an RNA stabilization solution configured to lyse red blood cells and stabilize RNA immediately after collection in the first vacuum-assisted blood collection container for pre-processing of a gene expression assay;

wherein the second vacuum-assisted blood collection container comprises a pre-processing agent that is a cell culture medium configured to initiate a blood cell culture immediately after collection and during a transport time for pre-processing of a cell culture based assay, including a cytokinesis-block micronucleus (CBMN) assay to decrease a sample processing time at a laboratory.

* * * * *